United States Patent
Pollack et al.

(10) Patent No.: US 9,835,637 B2
(45) Date of Patent: Dec. 5, 2017

(54) VIRTUAL SAMPLE QUEUES

(71) Applicants: Benjamin Samuel Pollack, Budd Lake, NJ (US); Colin Mellars, Dover, NJ (US); Baris Yagci, Whippany, NJ (US)

(72) Inventors: Benjamin Samuel Pollack, Budd Lake, NJ (US); Colin Mellars, Dover, NJ (US); Baris Yagci, Whippany, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/390,337

(22) PCT Filed: Apr. 1, 2013

(86) PCT No.: PCT/US2013/034779
§ 371 (c)(1),
(2) Date: Oct. 2, 2014

(87) PCT Pub. No.: WO2013/151920
PCT Pub. Date: Oct. 10, 2013

(65) Prior Publication Data
US 2015/0118756 A1    Apr. 30, 2015

Related U.S. Application Data

(60) Provisional application No. 61/619,173, filed on Apr. 2, 2012.

(51) Int. Cl.
*G01N 35/10* (2006.01)
*G01N 1/31* (2006.01)
*G01N 35/00* (2006.01)

(52) U.S. Cl.
CPC ..... *G01N 35/0092* (2013.01); *G01N 35/0095* (2013.01); *G01N 2035/0094* (2013.01); *Y10T 436/11* (2015.01)

(58) Field of Classification Search
CPC ........... G01N 35/0092; G01N 35/0099; G01N 35/00029; G01N 35/10; G01N 35/00584; G01N 35/00; G01N 1/312; G01N 1/31; G01N 1/30; G01N 1/28; G01N 1/00; Y10T 436/11; Y10T 436/00

USPC .......................................................... 436/43
See application file for complete search history.

(56) References Cited

U.S. PATENT DOCUMENTS

| | | | |
|---|---|---|---|
| 5,623,415 | A | 4/1997 | O'Bryan et al. |
| 5,827,478 | A | 10/1998 | Carey et al. |
| 2005/0220670 | A1* | 10/2005 | Palmieri ............ G01N 35/0092 422/64 |
| 2005/0220671 | A1 | 10/2005 | Stein et al. |
| 2007/0020764 | A1 | 1/2007 | Miller |
| 2008/0020469 | A1 | 1/2008 | Barnes et al. |

FOREIGN PATENT DOCUMENTS

| | | |
|---|---|---|
| EP | 1 881 329 A2 | 1/2008 |
| JP | H08-278310 A | 10/1996 |
| JP | H09-281113 A | 10/1997 |
| JP | H10-090276 A | 4/1998 |
| JP | H10-282115 A | 10/1998 |
| JP | 2001-004639 A | 1/2001 |
| JP | 2008-032711 A | 2/2008 |
| JP | 2011-525243 A | 9/2011 |
| JP | 2011-242154 A | 12/2011 |
| WO | 2011-093442 A1 | 8/2011 |

OTHER PUBLICATIONS

PCT International Search Report and Written Opinion dated Jul. 5, 2013 (10 Pages).
Supplementary EP Search Report dated Oct. 26, 2015 of corresponding European Application No. 13772368.0, 3 Pages.

\* cited by examiner

*Primary Examiner* — Christine T Mui

(57) ABSTRACT

Methods and systems can implement queues for an automation system that services a plurality of modules connected to one another by a transport mechanism, a processor can determining a desired queue for a module. An IVD analyzer can include an automation system, a plurality of stations configured to interact with objects transported by the automation system, and one or more processors that maintain a plurality of queues for at least a subset of the plurality of stations in memory and assign a plurality of the objects to each of the plurality of queues. Objects assigned to each of the plurality of queues need not be located physically proximate to a station associated with each of the plurality of queues.

18 Claims, 13 Drawing Sheets

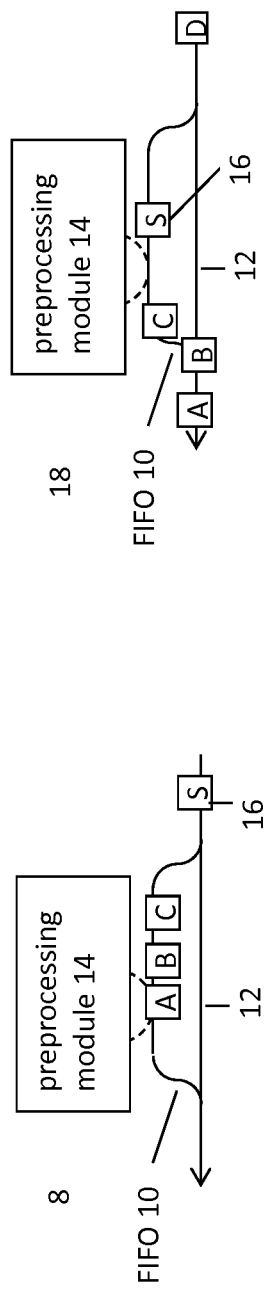
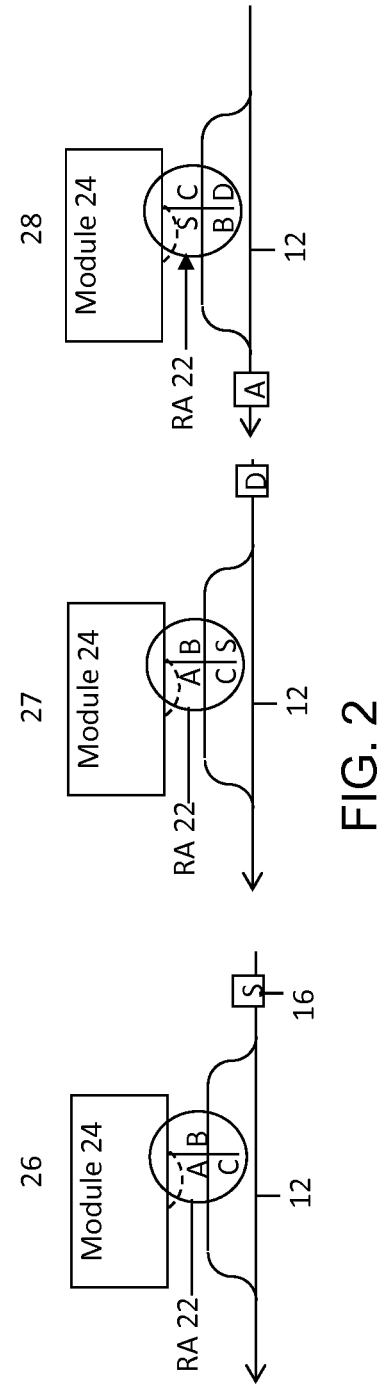
FIG. 1
FIG. 2

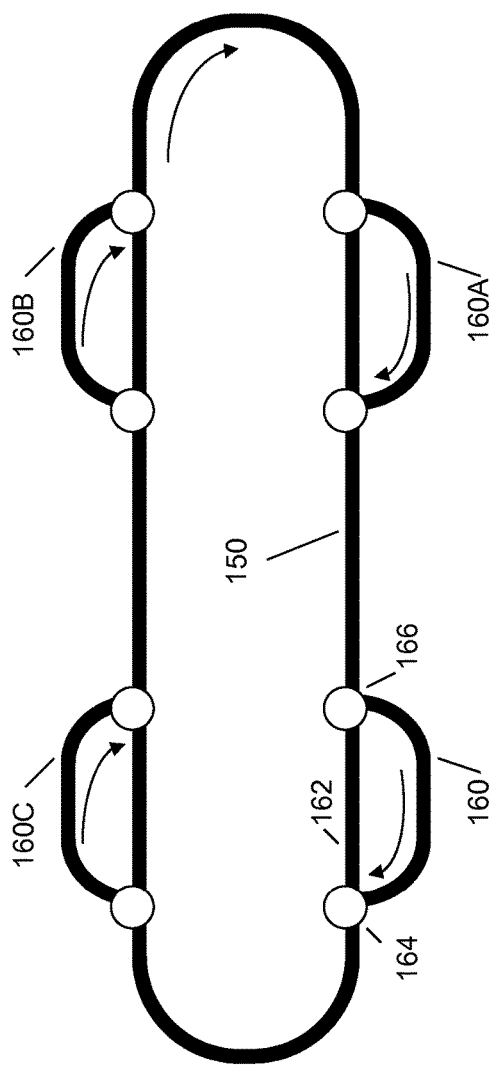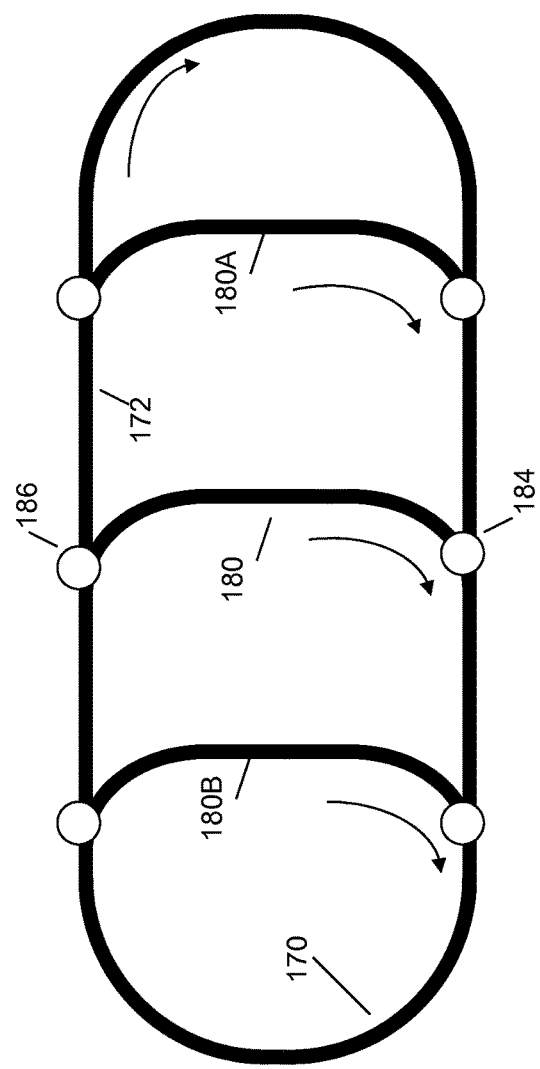

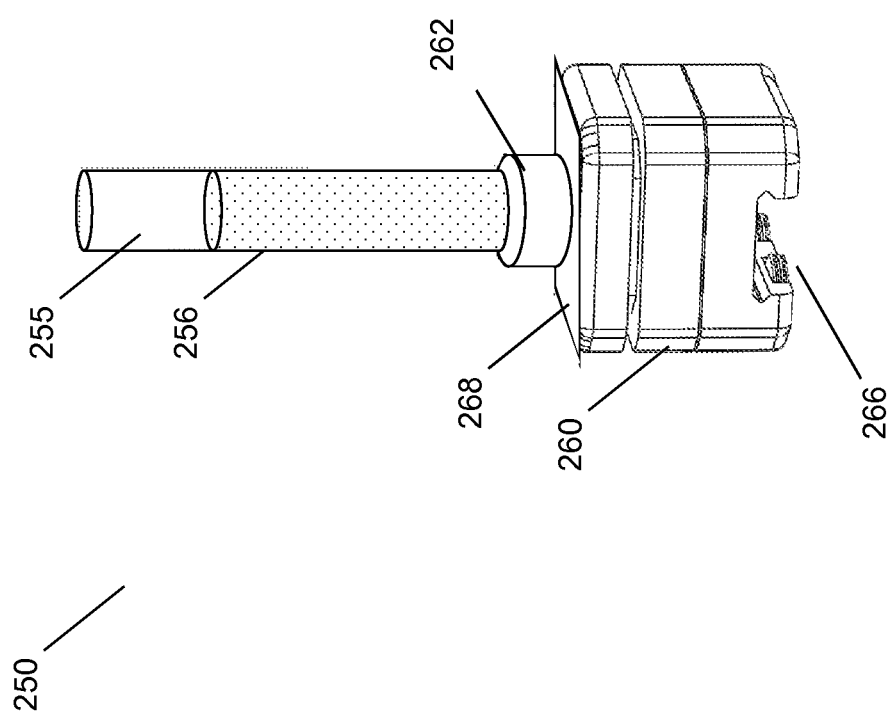

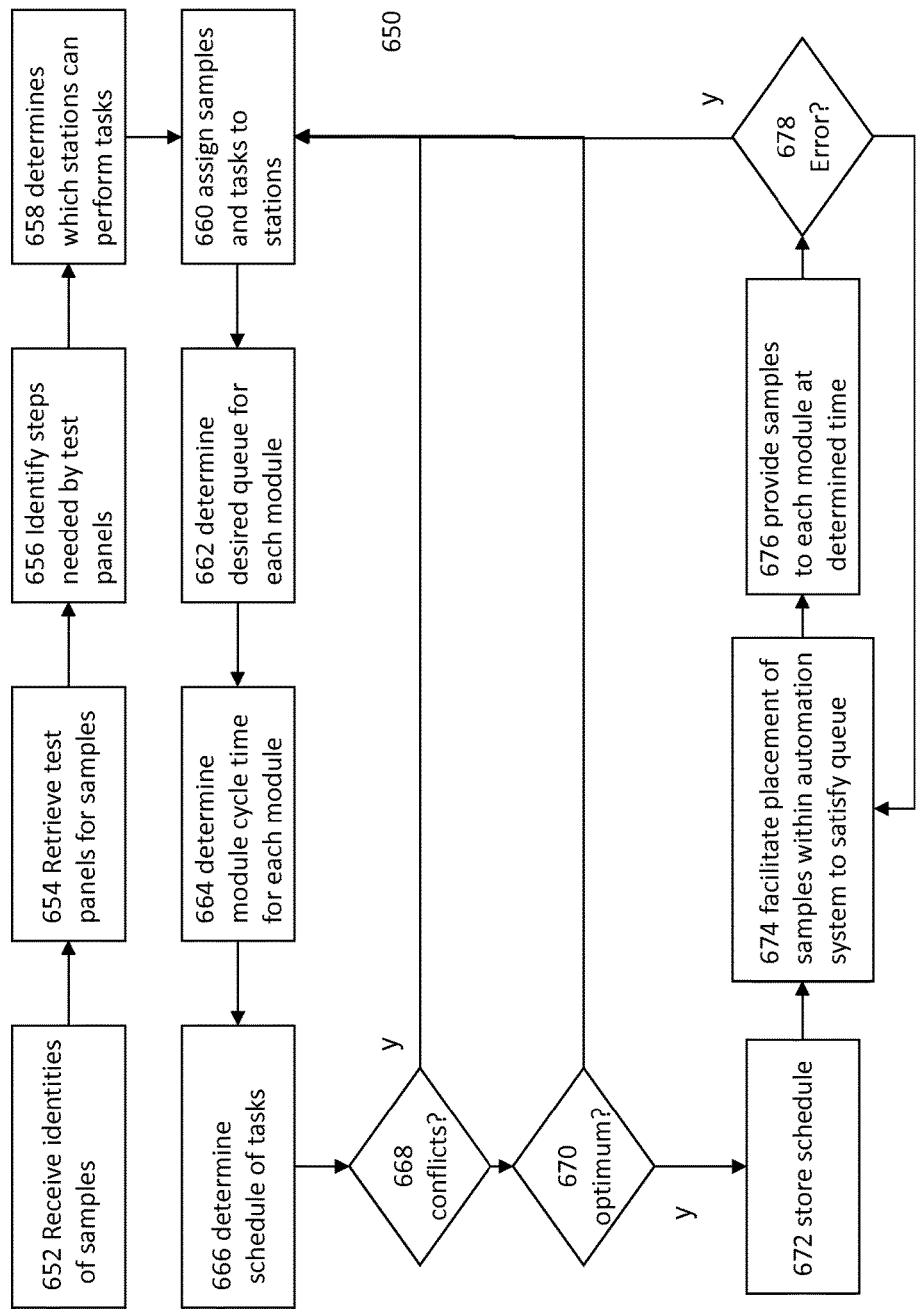

VIRTUAL SAMPLE QUEUES

CROSS-REFERENCE TO RELATED APPLICATIONS

This application claims priority to U.S. provisional application Ser. No. 61/619,173 filed Apr. 2, 2012, which is incorporated herein by reference in its entirety.

TECHNOLOGY FIELD

The present invention relates in general to an automation system for use in a laboratory environment and, more particularly to systems and methods for scheduling samples within the automation system by providing queuing logic. Embodiments of the present invention are particularly well suited, but in no way limited, to automation systems for use in an IVD environment.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials containing patient samples have been loaded. The analyzer extracts a liquid sample from the vial and combines the sample with various reagents in special reaction cuvettes or tubes (referred to generally as reaction vessels). In some conventional systems, a modular approach is used for analyzers. A lab automation system can shuttle samples between one sample processing module (module) and another module. Modules may include one or more stations, including sample handling stations and testing stations (e.g., a unit that can specialize in certain types of assays or can otherwise provide testing services to the larger analyzer, which may include immunoassay (IA) and clinical chemistry (CC) stations. Some traditional IVD automation track systems comprise systems that are designed to transport samples from one fully independent module to another standalone module. This allows different types of tests to be specialized in two different stations or allows two redundant stations to be linked to increase the volume of sample throughput available. These lab automation systems, however, are often bottlenecks in multi-station analyzers. Relatively speaking, traditional lab automation systems lack large degrees of intelligence or autonomy to allow samples to independently move between stations.

In an exemplary prior art system, a friction track, much like a conveyor belt, shuttles individual carrier mechanisms, sometimes called pucks, or racks of containers between different stations. Samples may be stored in sample containers, such as test tubes that are placed into a puck by an operator or robot arm for transport between stations in an analyzer along the track. This friction track, however, can only move in one direction at a time and any samples on the track will move in the same direction at the same speed. When a sample needs to exit the friction track, gating/switching can be used to move individual pucks into offshoot paths. A drawback with this set up is that singulation must be used to control the direction of any given puck at each gate and switch. For example, if two pucks are near one another and only one puck should be redirected into an offshoot path, it becomes difficult to control a switch so that only one puck is moved into the offshoot path and ensure that the proper puck is pulled from the friction track. This has created the need in many prior art systems to have pucks stop at a gate so that individual pucks can be released and switched one at a time at each decision point on a track.

Hard singulation slows down the overall track and increases traffic jams within the track. This leads to the need for physical queues within the track. Much like traffic on a road, traffic on the track causes an accumulation of slow-moving pucks because most of the time spent in transit during operation can be spent waiting through a line at a singulation point for switching by a gate. This leads to inefficiency in transit. Ultimately for a high volume analyzer, a substantial amount of time for each sample is spent waiting in queues at the gates on the friction track. This increases the latency experienced by each sample. Latency can be a problem for certain types of samples, such as whole blood samples, which can begin to separate or coagulate if the sample sits in the sample tube for too long.

Because pucks traditionally stop to be routed, handled, and processed, samples in prior art systems find themselves waiting in several queues before all processing on a sample is completed. This can result in large amounts of wasted space, as samples are essentially stored on the automation track as they await processing. Most conventional lab automation tracks maintain FIFO processing queues to buffer samples that are waiting to be processed by modules (analyzers or pre/post analytic devices). These buffers allow the track to process tubes at a constant rate even though the modules create bursts of demand. They can also substantially increase the throughput of the individual modules by allowing them to perform preprocessing tasks for future samples, (e.g., prepare a cuvette or aspirate reagent, while processing the current sample.

Another problem with long queues and traffic on the friction track is the issue of handling STAT samples. A STAT sample is a sample that an operator wishes to have moved to the front of the line so that results for that sample can be returned quickly. For example, in a hospital with an emergency room, test results may be urgent for a patient awaiting treatment. In prior art friction track systems with long queues, the entire queue often must be flushed to make way for the STAT sample. This can undo several minutes worth of sorting of samples and can increase the overall latency experienced by non-STAT samples.

SUMMARY

Embodiments of the present invention may address and overcome one or more of the above shortcomings and drawbacks by providing devices and systems for transporting samples by utilizing virtual queues in software to avoid requiring that a sample be physically waiting at a processing station before it is needed.

According to one embodiment of the invention, a method implements queues for an automation system that services a plurality of modules connected to one another by a transport mechanism, such as an automation track and carriers. Each of the plurality of modules is configured to process samples, while the transport mechanism is configured to transport the samples between the plurality of modules within a system cycle time. The method includes determining a desired queue for a module, wherein the desired queue comprises an ordering of at least one sample to be processed by the module and determining a module cycle time for the module, wherein the module cycle time comprises a length of time needed by the module for processing one of the at least one sample. The method further includes facilitating placement of the at least one sample in the automation system to satisfy the desired queue for the module, wherein the at least one sample is placed to reach the module at a determined time based on the ordering of the at least one sample in the desired queue and the module cycle time and providing the at least one sample to the module at the determined time. According to one aspect of some embodiments, the system cycle time can include an amount of time for processing a sample by one of the plurality of modules and an amount of time for transporting the sample between two of the plurality of modules. According to another aspect of some embodiments, the automation system can include one or more holding buffers configured to hold one or more of the at least one sample. Each of the plurality of modules can include a module holding area configured to hold one or more of the at least one sample. According to another aspect of some embodiments, placement of samples can include moving the at least one sample to at least one of: (i) a location along the transport mechanism, (ii) at least one of one or more holding buffers, (iii) at least one of a plurality of module holding areas, and (iv) another of the plurality of modules.

According to one aspect of some embodiments, the method can further include assigning a priority level to the module, comparing the priority level of the module to that of a second module upon occurrence of a conflict for the at least one sample between the module and the second module, and providing the at least one sample to the module or the second module based on the compared priority level. According to another aspect of some embodiments, the method can further include moving at least one sample in the automation system to account for a STAT sample, wherein the movement of the sample allows for the desired queue to be satisfied after processing of the STAT sample, and providing the STAT sample to the module for processing thereof.

According to one aspect of some embodiments, at least a subset of the plurality of modules can include in vitro diagnostics modules, where each sample is a sample. According to another aspect of some embodiments, the plurality of modules can include one or more of: (i) a sample handling module configured to add and remove the at least one sample to and from the transport mechanism, (ii) an immunoassay module, and (iii) a clinical chemistry module. According to another aspect of some embodiments, queues can include a first-in first-out queue or a random-access queue.

According to another one embodiment of the invention, an automation system for implementing queues includes a plurality of modules, each of the plurality of modules configured to process samples and a transport mechanism configured to transport the samples between the plurality of modules within a system cycle time, the transport mechanism connecting the plurality of modules to one another. A schedule controller can be configured to process instructions to implement the methods described herein.

According to another one embodiment of the invention, an analyzer for use in in vitro diagnostics includes an automation system, a plurality of stations configured to interact with objects transported by the automation system, and one or more processors. The processor maintains a plurality of queues for at least a subset of the plurality of stations in memory and assigns a plurality of the objects to each of the plurality of queues. Objects assigned to each of the plurality of queues need not be located physically proximate to a station associated with each of the plurality of queues. Objects may include patient samples or other objects described throughout.

According to one aspect of some embodiments, the processor can be further configured to assign individual objects to multiple queues simultaneously and/or configured to verify that each object can physically reach the station associated with each of the plurality of queues to which the object is to be assigned within a time period needed by the queue. According to another aspect of some embodiments, the plurality of queues include at least one FIFO queue or at least one random access queue.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 1 is a diagrammatic view illustrating multiple situations in an exemplary physical FIFO queue;

FIG. 2 is a diagrammatic view illustrating multiple situations in an exemplary physical random access queue;

FIGS. 4A and 4B are diagrammatic views of track geometries that can be used with the automation system embodiments disclosed herein;

FIG. 6A is a perspective view of an exemplary carrier that can be used with the embodiments disclosed herein;

FIG. 12 is a flow diagram showing the operation of the virtual queues in certain embodiments.

DETAILED DESCRIPTION OF ILLUSTRATIVE EMBODIMENTS

Figure 3:
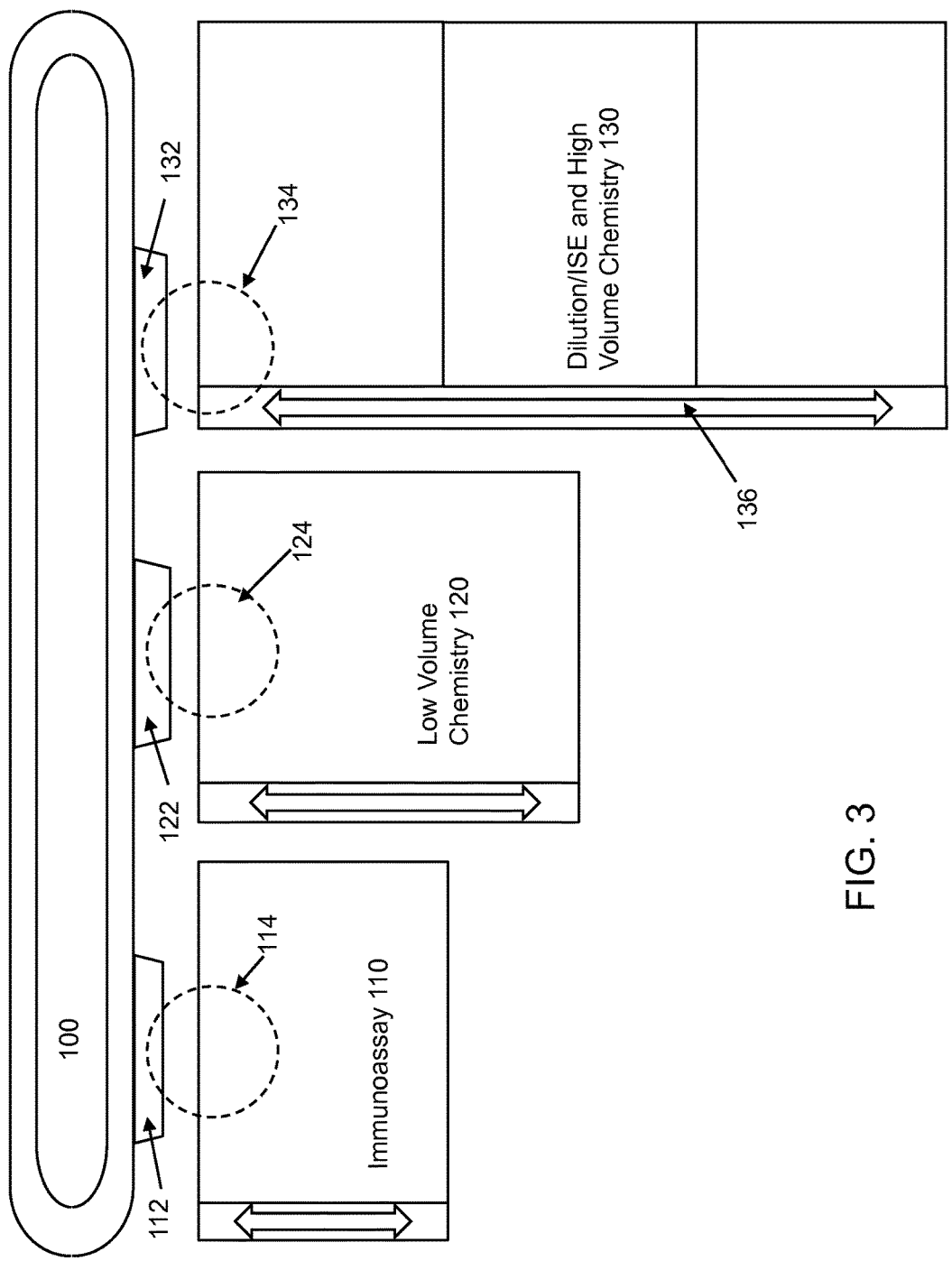
FIG. 3 is a top view of an exemplary clinical chemical analyzer geometry that can be improved by use of the automation system embodiments disclosed.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

Carriers/Trays/Racks: A carrier may be distinguishable from a tray, which may commonly refer to a device that does not travel along an automation track (e.g., carried by an operator) and is configured to hold a plurality of payloads (e.g., sample tubes). A rack is a general term to describe a device that is configured to hold a plurality of payloads (e.g., sample tubes). A rack may refer to a tray (when used outside an automation track) or carrier (when configured to traverse an automation track) that is configured to carry a plurality of payloads. Racks may refer to one-dimensional or two-dimensional arrays of slots, in some embodiments.

Central controller or processor: A central controller/processor (which may sometimes be referred to as a central scheduler) is a processor that is part of the automation system, separate from any processors onboard carriers. A central controller can facilitate traffic direction, scheduling, and task management for carriers. In some embodiments, a central controller can communicate with subsystems in the automation system and wirelessly communicate with carriers. This may also include sending trajectory or navigational information or instructions to carriers and determining which carriers should go where and when. In some embodiments, local processors may be responsible for managing carriers on local track sections, such as managing local queues. These local processors may act as local equivalents to central controllers.

Decision point: Decision points are points on an automation track where different navigational or trajectory decisions may be made for different carriers. A common example includes a fork in a track. One carrier may proceed without turning, while another may slow down and turn. Decision points may include stopping points at instruments, where some carriers may stop, while others may proceed. In some embodiments, deceleration zones ahead of turns may act as decision points, allowing carriers that will be turning to slow down to limit lateral forces, while others may proceed if not turning or if the motion profile for that carrier does not require slowing down. The decisions made at decision points can be made by processors onboard carriers, processors local to the track section, a central processor, or any combination thereof, depending on the embodiment.

Independent carrier: In some embodiments, carriers may be characterized as independently controlled carriers. Independently controlled carriers are carriers with independently controlled trajectories. In some embodiments, independent carriers may be operating at the same time, on the same track, with carriers carrying one or a plurality of combinations of payloads that differ by size, weight, form factor, and/or content. The trajectories of each independently controlled carrier may be limited by a motion profile that includes; maximum jerk, acceleration, direction, and/or speed for the carrier while moving in the automation system. The motion profile can limit or define the trajectory for each carrier independently. In some embodiments, a motion profile can be different for different sections of the automation system (e.g., in straight track sections vs. around curves to account for the added lateral forces while turning), for different carrier states (e.g., an empty carrier may have a different motion profile from a carrier transporting a sample or from a carrier transporting a reagent or other item), and/or for different carriers. In some embodiments, carriers can include onboard propulsion components that allow individual carriers to independently operate responsive to a motion profile or trajectory or destination instructions intended for each separate carrier.

Intelligent carrier/semi-autonomous carriers: In some embodiments, carriers may be characterized as intelligent carriers. An intelligent carrier is a carrier with onboard circuits that participates in motion, routing, or trajectory decisions. An intelligent carrier can include digital processors that execute software instructions to proceed along an automation surface responsive to the instructions or onboard analog circuits that respond to motion input (e.g., line follower circuits). Instructions may include instructions characterizing motion profiles, traffic, or trajectory rules. Some intelligent carriers may also include onboard sensors to assist onboard processors to route the carrier or make decisions responsive to the carrier's environment. Some intelligent carriers may include onboard components, such as motors or magnets, which allow the carrier to move responsive to control of an onboard processor.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. WD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Landmarks: In embodiments where carriers include onboard sensors, optical or other marks in track surfaces or locations viewable/sensible from track surfaces can act as landmarks. Landmarks can convey geographic information to carriers, such as a current location, upcoming stopping location, decision point, turn, acceleration/deceleration points, and the like.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/ vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Pullouts, sidecars, offshoot paths: These terms may be used to refer to track sections that are off the main portion of a track system. Pullouts or sidecars may include chords, parallel tracks, or other suitable means for separating some carriers from a primary traffic pattern. Pullouts or sidecars may be configured to facilitate physical queues or allow certain carriers to stop or slow down without disrupting traffic on a main track section.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

STAT (short turnaround time) sample: Samples may have different priority assigned by a laboratory information system (LIS) or operator to assign STAT priority to samples that should take precedent over non-STAT samples in the analyzer. When used judiciously, this may allow certain samples to move through the testing process faster than other samples, allowing physicians or other practitioners to receive testing results quickly.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

Exemplary Embodiments

One or more of the problems commonly associated with physical queues in the prior art may be resolved or mitigated by using embodiments of the invention, by utilizing virtual queues. Physical queues used in the prior art generally do not differentiate between buffers and logical queues. That is, each queue within a prior art analyzer requires the physical presence of each sample in the logical queue. In fact, the logical queue is not distinguishable from the physical space for queue. For each sample into the logical queue, that sample is physically placed into space taken by that queue. This results in a buffer for each queue. Buffers may be useful for situations where arrivals into a queue are not coincident with when a sample will be utilized. Buffers allow stations to operate at their own pace, without requiring that samples arrive at that same rate. Sample arrivals into queues may be erratic, arriving in bursts at busy times in the analyzer. Meanwhile, processing stations typically operate at a fixed rate.

Generally, placing a sample in a physical queue is helpful, because it guarantees that the sample will be available when the station utilizing the queue needs the sample. That is, by placing a sample in a physical queue, it guarantees that when the sample reaches the head of the logical queue, the sample will be physically available. Because traditional queues do not differentiate between a physical and logical queue, this guarantee is necessarily met by the sample being placed into the queue.

However, when the physical and logical queues are the same, it means that a sample must be physically ready to be placed in it to the queue before the sample is needed. This results in increased latency within the system, as each sample must arrive at a queue before it is needed, and wait. This causes the turnaround time for each sample to be increased, as much of the time spent in the automation system by a sample is spent waiting, rather than moving or being processed. This can also waste valuable space, as the automation system must be scaled such that a substantial number of samples are on the automation system waiting. This results in traffic and inefficiencies. Furthermore, if a sample is both physically resident and logically in a queue, that sample cannot be physically resident elsewhere. Accordingly, that sample cannot be in multiple queues at once. This rule, when using physical queues, must be considered when scheduling tasks within the automation system. A sample cannot be in two places at once, and therefore cannot be placed into a queue until a previous queue has released that sample.

Embodiments of the present invention may address one or more of these issues by lowering or removing the entanglement between physical presence and logical queues. In some embodiments, virtual queues are used. As used herein, virtual queues refer to queues that are maintained in software as logical structures, or as part of a scheduling algorithm, without requiring each sample that is in a logical queue to be placed in a physical relationship within a physical queue. In some embodiments, a sample may be substantially non-proximate or anywhere in the automation system while being logically in a virtual queue associated with a single location within the automation system. For example, a pipetting station may have a logical queue that it uses to request and process samples. Samples within this logical queue need not be physically present at the pipetting station, allowing of those samples to be moving within the automation system while in the logical queue. In some embodiments, those samples can be actively traversing other sections of the automation system while in that queue, such as sitting in a track portion associated with another station. This may be advantageous, by allowing samples to be placed into a logical queue before they physically arrive at any processing station. This may reduce the amount of space needed to store samples at that station, as samples in the logical queue need not be physically accommodated before they reach the head of the queue. Furthermore, in some embodiments, samples may be resident in multiple logical queues, allowing multiple handling stations to consider these samples as available, without limiting the ability of the sample to be processed by other stations in the meantime.

There are two traditional types of queues. These queues are traditionally physical, but these queues may be implemented logically for use with some embodiments. A first type of queue is a FIFO queue. The FIFO queue operates substantially like a buffer, introducing a delay between a sample arriving versus when it is processed. Samples are made available to each station that has a FIFO queue in a fixed order. Once a sample has been made available, the station processes that sample, and releases that sample. That sample will not be used again by that station. If a station is operating at a fixed rate, such as processing one sample for each time, the amount of time that will pass before a sample is placed at the end of the queue and when that sample reached the head of the queue can be easily determined. If a sample is at position and in the queue, the sample will be needed by the station and cycles later. In some embodiments, scheduling software takes advantage of this time and position relationship.

However, FIFO queues may not be suitable for all queues in the analyzer. While the rigid predictability of FIFO queues enables the parallelization of some processing tasks, it also prevents the modules from using opportunistic scheduling that requires the reordering of tests. For example, the internal resource conflicts of most immunoassay analyzers can require interleaving the tests from multiple samples in order to reach maximum efficiency, allowing first steps on a second sample to begin before the final steps on a first sample. A FIFO queue, when implemented with a physical buffer, can reduce the throughput of these analyzers by as much as 20%. Another problem with FIFO queues can be their inability to handle priority samples.

A FIFO queue is most suitably used by processing modules that perform preprocessing or post-processing tasks (such as a capper or decapper), but may also be used for processing tasks that can tolerate a fixed order of samples (e.g., tests where a single aspiration will be performed). A station utilizing a FIFO queue should be able to operate while the order of samples and timing at which samples will reach the head of the queue are fixed once a sample has been placed in the FIFO queue.

A random-access queue, on the other hand, allows a station to request samples out of order within the queue. Without some knowledge of the order in which a station plans on handling samples in its queue, it may be impossible to predict when a sample will be needed by the station. A sample within a random-access queue may be requested multiple times. Ideally, once a sample is placed in a random-access queue, the station utilizing the queue assumes that it can access the sample at any time, accessing samples in any order, as often and frequent as it likes, and maintains control of each sample in the queue until a sample is explicitly released by that station. Traditional physical random-access queues have utilized carousels to ensure that each sample remains in the queue for random-access and allows samples to be accessed in any order. Traditional physical random-access queues suffer from space constraints, as the size of a carousel will grow in proportion to the square of the number of samples, requiring a large amount of area for a moderate number of samples. Similarly, as the size of a queue rows, the larger carousel may need to move faster to accommodate the large number of samples that may need to be cycled through to provide random-access.

Accordingly, traditional random-access queues have been limited to only a few samples or have limited the extent to which samples may be randomly accessed. For example, in a pure random-access queue, any sample in the queue can be accessed at any time, providing no correlation between the current sample requested and the previous sample. However, similar to the principles of caching in a computer architecture, in some embodiments, there may be reasonable constraints that may be placed on random-access that may allow seemingly random-access without requiring every sample in the queue to be available during the next operation cycle. For example, if a sample queue has 20 samples in it, constraints may be tolerable where the next sample to reach the head of the queue is limited to one of the five nearest samples to the current sample in a carousel. This may provide random-access without providing random-access to all samples within a queue for the next cycle. This may be referred to as a partial random-access queue. This concept may be utilized by some random-access queues utilized in some embodiments.

A physical random-access queue may have the following disadvantages: it may increase complexity/cost and reduces reliability; it may increase the steady-state processing time, because the sample must be transferred into and out of the random-access queue (processing delays are implementation dependent); it may increase the physical footprint of the track (e.g., the diameter of the carousel will increase with the number of samples it is designed to hold); it may prevent the queue from being quickly flushed if the module goes offline, in most implementations.

FIG. 1 illustrates a FIFO queue in action. FIFO queue 10 is placed on a sidecar off of the main track 12. Samples moving along main track 12 move in the direction of the arrow. In situation 8, three samples, A, B, and C, are in FIFO queue 10. Sample A is at the head of the queue and is being processed by preprocessing module 14. Module 14 may be a station, such as a decapper, that processes samples in the order in which they arrive. Meanwhile, STAT sample 16 arrives along main track 12 and enters FIFO queue 10. In situation 18, FIFO queue 10 is flushed. While sample A has finished processing, samples B and C must be flushed to expedite the processing of STAT sample 16. Samples B and C must then traverse the entire automation system or a loop within the automation system to be placed back into FIFO queue 10. Meanwhile, sample D arrives along track 12 to be placed into FIFO queue 10. Depending on the requirements of preprocessing module 14, the original order may have significance, in which case samples B and C must make another circuit of the automation system before entering the FIFO queue. In some embodiments, preprocessing module 14 can accommodate the change in the order of the FIFO queue, allowing sample D to be placed in the queue behind the STAT sample 16, which will enable sample D to be processed before samples B and C.

FIG. 2 illustrates a random-access queue in action. Random-access queue 22 is a physical random-access queue that includes four positions in a carousel. Module 24 is given access to samples in the queue by rotating the carousel so that the desired position aligns with a pipette in module 24. Samples travel along main track 12 in the direction of the arrow, and samples to be processed by module 24 are directed into a sidecar that places samples into the random-access carousel. Module 24 may be, for example, an analyzer testing station. In situation 26, samples A, B, and C are placed in the random-access carousel 22. Meanwhile, a STAT sample 16 arrives along main track 12 to be processed by module 24. In situation 27, module 24 completes processing of sample A, while placing STAT sample 16 into an empty slot in the carousel. Sample D arrives along main track 12 for processing. In situation 28, sample A completes processing allowing another sample to move to the head of the queue for processing by module 24. In this instance, the STAT sample is given priority. Carousel 22 moves the STAT sample into position for interaction with module 24. Sample D may be placed into the empty slot left by sample A. It should be noted that in this situation, samples B and C are not flushed, because STAT sample 16 can be accommodated by the carousel and be moved to allow the STAT sample to be processed before samples B and C. Furthermore, because samples B and C remain resident in the random-access queue, module 24 can decide whether to process samples B and C ahead of sample D, depending on the local scheduling algorithms used by module 24 to facilitate tests on the samples.

Embodiments of the present invention may provide all or a subset of the functionality of the queues illustrated in FIGS. 1 and 2 by decoupling physical queues from logical queues. That is, the functionality of random-access and FIFO queues may be provided by maintaining logical queues having these qualities, without requiring that samples in the queue be physically adjacent and stored while waiting for their turn at the head of the queue. For example, a virtual FIFO queue in software may allow samples to be in a different part of the analyzer automation system before they reach the head of the queue. This may be militated by the fact that samples in a FIFO queue have a predetermined order and therefore a determinable time at which a sample will reach the head of the queue based on their position in the logical queue. Before a sample reaches the head of the queue in a FIFO queue, that sample may be used for other tasks within the automation system, such as processing by other stations. For example, a software FIFO queue may allow a sample to be in both a FIFO queue for a testing station and a FIFO queue for a decapper station. Because the order of operations within the analyzer ensures that a sample will be preprocessed added to capper station before being processed by a testing station, the sample may be placed in both virtual queues, provided that it can be determined that the sample will be processed by reaching the head of the queue of the decapper station and have sufficient time to move over to the testing station before that sample reaches the head of the logical queue for the testing station.

Virtual random-access queues can operate in a similar manner. Whereas prior art systems typically require a sample be physically placed in a queue mechanism, such as a carousel, a sample may be resident in a virtual random-access queue and be physically located at any reasonable place in the automation system provided that the automation system can guarantee that the sample can be placed into position for interaction with an instrument when that instrument requests the sample be at the head of the random-access queue.

This can be accomplished by utilizing automation systems that provide reliability and determinability while samples are in the automation system. Most conventional automation systems that utilize friction tracks and sample pucks that must be singulated an identified at each junction may not provide enough repeatability or reliability to allow virtual queues to be separate from physical queues. In traditional IVD automation systems, traffic within the automation system makes it difficult or impossible to determine with reliability when a sample, currently located at one portion of the automation system, can be available at a location elsewhere in the automation system. Performance bottlenecks, such as buffers created by each singulation point within the automation system make the latency required for a sample to move between two points of the automation system difficult. In some embodiments, the automation systems disclosed herein may resolve some or all of this unreliability, facilitating the use of virtual queues that are not limited by physical queues. Accordingly, virtual queues can be maintained in software, without requiring samples be physically proximate to a station associated with the queue at all times while that sample is in the queue.

Some embodiments of the present invention include systems and methods that provide a more efficient lab automation system to allow samples to be shuttled between and amongst various analyzer testing stations with less latency and more individual control. Embodiments of the present invention can reduce or eliminate queues experienced by samples traversing the automation system. Usually, samples need to undergo many different types of testing in an automated clinical analyzer (analyzer), which may not be available in a single testing station. Testing stations within an analyzer can be adapted for specialized testing. For example, immunoassays may be performed by an immunoassay station that includes certain incubation capabilities and uses specific reagents that are unique to immunoassays. Chemical analysis can be performed by a clinical analyzer and electrolyte chemistry analysis can be conducted by an ion-selective electrode (ISE) clinical analyzer. By using this modular approach, an analyzer can be adapted not only to the types of testing being done on samples, but also the frequency and volume of testing necessary to accommodate the needs of the lab. If additional immunoassay capability is needed, a lab may choose to add additional immunoassay stations and increase overall throughput for immunoassay testing in their system.

An exemplary track geometry, for use in transporting samples within an analyzer typical in prior art configurations, is shown in FIG. 3. This track can include prior art friction tracks, which may introduce problems in designing a track system. However, certain embodiments of the present invention could also use a similar geometry without necessarily employing a friction track for motion. Track 100 can be a generally oval-shaped track that conveys samples in pucks or trays between various stations, such as sample preparation or analyzing/testing stations 110, 120, and 130. Track 100 could be a single direction track or, in some instances, a linear bidirectional track. In this exemplary set-up, each analyzer 110, 120, 130 is serviced by a respective sidecar 112, 122, 132. At the junction between the track 100 and each sidecar, a gate or switch can be placed that allows samples to be diverted to or from track 100 to the sidecar. The oval nature of track 100 can be used to circulate samples while they wait for access to each analyzer. For example, analyzer 110 may have a full queue in sidecar 112, such that new samples on track 100 cannot be diverted to pullout 112 until analyzer 110 finishes handling a pending sample in sidecar 112 and inserts it back into the main traffic flow of track 100.

In some prior art systems, each sidecar can be serviced by a handling mechanism such as sample probe arms 114, 124, and 134. These robotic handling arms can aspirate sample material from samples in a sidecar via a probe needle, or can pick up a sample tube from the sidecar and transport it into the corresponding testing station. In this exemplary system, the available testing stations include an immunoassay station 110, a low-volume chemistry station 120, and an expandable dilution/ISE electrolyte and high-volume chemistry station (or stations) 130. Some advantages of this approach are that the track 100 can be part of a separate lab automation system that can be added onto otherwise self-contained stations, and the track 100 and stations 110, 120, and 130 can be independently upgraded, purchased, or serviced. Some stations, such as high-volume chemistry station 130, can include their own friction track 136 that operates independently of track 100. Friction track 136 can include a bidirectional friction track that allows samples to move between sub-modules of high-volume chemistry station 130. A drawback of this type of system is that the separate friction tracks operate independently and, control of overall automation becomes more complicated. Furthermore, transitions between friction tracks 136 and 100 can be slow and cumbersome, particularly where there is no direct route between two friction tracks. In some systems, moving between tracks may require lifting and placing samples via a robot arm.

Prior art lab automation systems for analyzers generally treat individual analyzer/testing stations as generic destinations for a sample on the track. In some embodiments of the present invention, the lab automation system can be integrated within the individual testing stations, which can substantially reduce or eliminate the complexity of the individual testing stations and reduce the need for separate sample handling systems within each station. In some embodiments, by integrating the lab automation system into the stations, the system can begin to treat individual stations less as generic destinations and more as portions of a multi-route track onto which a sample can travel.

FIG. 4A shows one embodiment of a track system that can be adapted for use with the present invention. Track 150 is a rectangular/oval/circular track on which sample carriers move in a clockwise (or counterclockwise) direction. Track 150 may be unidirectional or bidirectional. Carriers can transport any suitable payload with the IVD environment, such as fluid samples, reagents, or waste. Fluids, such as patient samples can be placed in a container or vessel, such as a test tube, vial, cuvette, etc. that can be transported by a carrier. Carriers, and by extension payloads such as samples, can move on the main track 150 or be diverted via decision points such as 164 or 166. These decision points can be mechanical gates (as in the prior art) or other mechanisms suitable for allowing a sample to be diverted from the main track 150 to a sidecar, such as 160, 160A, 160B, 160C as described herein. By way of example, if a sample carrier is traversing the main path 150 and reaches decision point 166, it can be made to continue on the main track to segment 162 or it can be made to divert to sidecar 160. The systems and methods by which the decision can be made to divert the sample carrier at decision point 166 are described throughout.

FIG. 4B shows an alternative track layout that may be suitable for certain embodiments of the present invention. Track 170 is also a generally circular track with sample carriers moving clockwise (or counterclockwise). In this example, rather than having sidecars outside of the track, pullouts 180, 180A, and 180B are chords within the track. Similarly, when sample carriers reach decision points, they may be diverted off of the main path to a side path, such as path 180. At decision point 186, a sample on the main track 170 can be made to continue on the main track or be diverted onto path 180. Once an analyzer station along handling path 180 is done processing the sample, the sample proceeds to decision point 184 where it may be placed back onto the main path 170.

Figure 5:
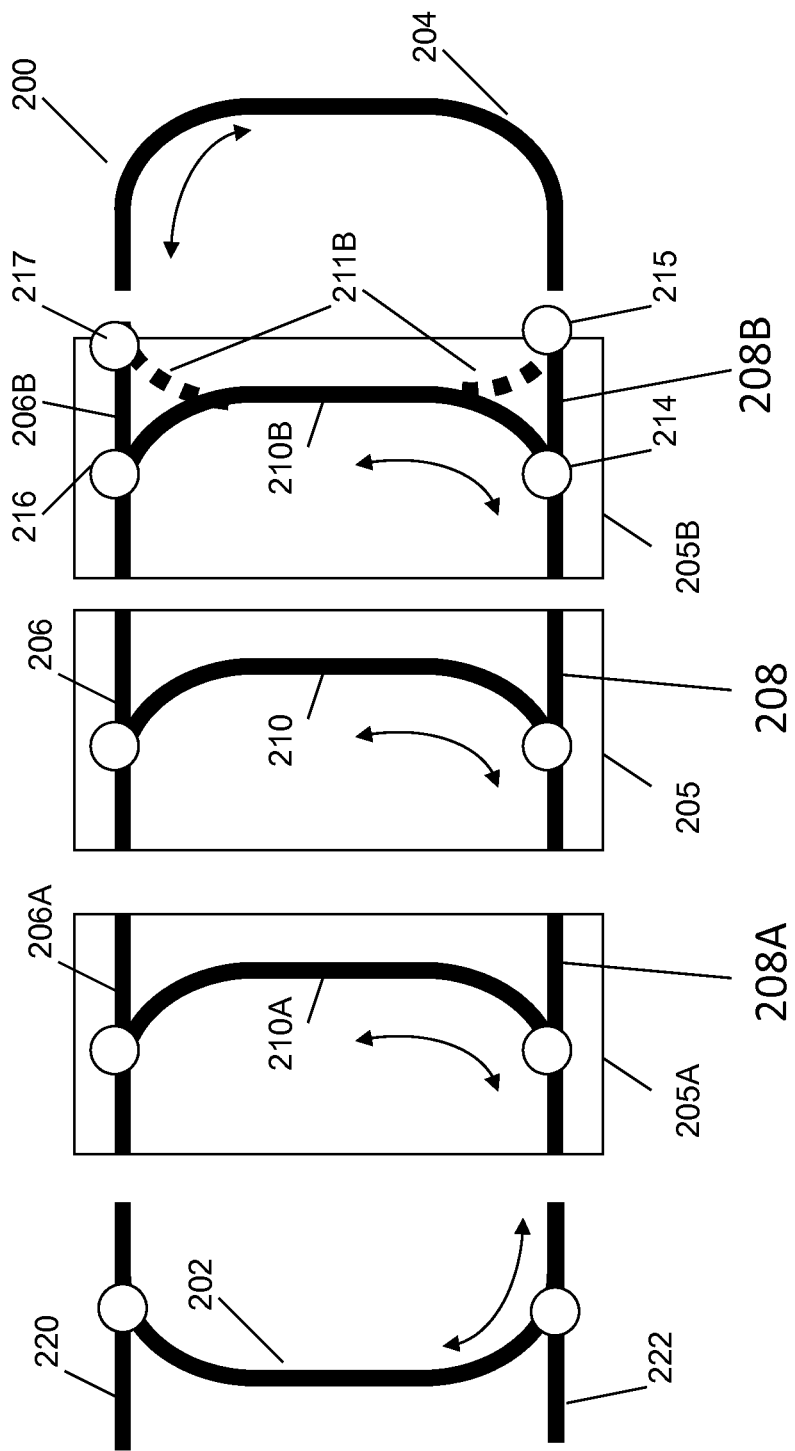
FIG. 5 is a diagrammatic view of an exemplary modular track configuration that can be used with the embodiments disclosed herein.

FIG. 5 shows a modular approach to the automation system track that can be used for certain embodiments of the present invention. In this example, the tracks may be integrated into individual analyzer stations, such that the track can be used as part of the internal motion or sample handling system of individual lab stations. In the prior art, it is common to have multiple different types of motion systems within different analyzer/testing stations. For example, some stations can include friction tracks for shuttling pucks or trays of sample tubes, and may include carousels containing smaller vessels, such as cuvettes and reaction vessels, into which portions of the sample can be aspirated and dispensed. In some embodiments, by integrating portions of the track system into the analyzer stations themselves, each station can include its own queuing logic and may be simplified to eliminate unnecessary internal motion systems.

With respect to FIG. 3, the track 200 can be broken into modular components that are integrated into analyzer modules. In this exemplary track, modules 205, 205A, and 205B can be combined with one another and optionally other modular track components 202 and 204 to form a track similar to that shown in FIG. 4B. For instance, 205A can be a module that performs the same function as immunoassay 110 (FIG. 3), 205 can be a module that performs the same function as low-volume chemistry module 120 (FIGS. 3), and 205B can be a module that performs ISE electrolyte testing, like module 130 (FIG. 3). In this example, the main outer track can be formed by track segments 202, 204, 206, 206A, 206B, 208, 208A, and 208B. Within the analyzer modules 205, 205A, and 205B, internal paths 210, 210A, and 210B form pullouts from the main track. The internal paths can be used for internal queuing and can be managed independently within each analyzer module to allow each module to have greater control over samples to be processed.

One advantage of integrating track 200 and sub-paths 210, 210A, and 210B into the analyzer modules 205, 205A, and 205B, respectively, is that the internal handling mechanisms within each analyzer module can be specially adapted to better coordinate with the track sub-paths. In some embodiments, modules 205, 205A, and 205B can be adapted to process each sample within a period that is less than an operation cycle of the overall analyzer, leaving enough time for the sample to be routed along the track system to another module after processing, allowing the other module to immediately process the sample on the next operation cycle. As used herein, an operation cycle is a unit of time used by scheduling algorithms to allot processing time to modules for sample assays. These can be dynamic or fixed and can allow synchronous operation of the modules in the analyzer and provide a reliable timing model for scheduling samples amongst multiple modules in the analyzer. The operation cycle time can be chosen to be the time needed by any given module between when it starts processing a first sample, and when it is ready to process another sample under expected steady-state conditions. For example, if an analyzer can process one test every three seconds, and the expected average tests per sample is seven, the operation cycle time can be 21 seconds. It should be understood that individual modules can implement efficiency techniques, such as parallelism or processing multiple samples within a cycle, to maximize throughput, even when the number of tests-per-sample varies from an expected amount. Furthermore, it should be understood that in some embodiments, individual modules have different operation cycle times, and these modules can operate substantially asynchronously from one another. Virtual queues or buffers can be used to assist the management of sample scheduling where cycle times or demand vary between modules.

Enabling transit between modules in the analyzer in a reliable time frame, on the order of a single operation cycle or less, achieves many performance advantages not possible with prior art track systems. If a sample can be reliably handled by an analyzer module and transported to the next analyzer module within a single cycle of the analyzer, traffic handling in queuing becomes much simpler, throughput becomes more consistent, and latency can be controlled and reduced. Essentially, in such an analyzer, a sample can reliably be handled by the track system and processed uniformly such that a sample does not sit idly on the track system waiting in queues. Furthermore, queues within the system, such as queues within a given analyzer module, can reliably be shortened, limited by the number of modules within the system.

If decision points such as 214 and 216 can be streamlined such that there is no need for a queue at each decision point, the only physical queues can be within sub-paths 210, 210A, and 210B. As described above, these can be treated as RA queues or FIFO queues. If a STAT sample is placed onto track 200, RA queues within sub-paths 210, 210A, and 210B need not be flushed, as the STAT sample can be processed immediately. Any FIFO queues can be individually flushed. For example, if a STAT sample is placed onto track 200 at section 222, the sample may be routed to the appropriate analyzer 205B via the outside track and decision point 216. If there are other samples (and by extension the sample carriers transporting those samples) waiting in the queue in path 210B, only those samples in the queue may need to be flushed to allow a STAT sample to take priority. If the outer track 200 is presumed to take less than an operation cycle to traverse, any samples that were flushed from the queue in 210B can simply be circulated around the track and placed immediately back into the queue in path 210B immediately behind the STAT sample, eliminating any down time caused by the STAT sample.

Entry paths 220 and 222 can be used to input samples to the track 200. For example, regular priority samples can be placed onto track 200 at input 220 and STAT priority samples can be placed on input 222. These inputs can be used as outputs for samples when complete, or other ports (not shown) can be used as the output paths for used samples. Input 220 can be implemented as an input buffer, acting as a FIFO queue for input samples seeking access to the track 200. Once a sample reaches the head of the queue at input 220, it can be moved onto the track (either by being placed in a carrier or by being placed in a carrier when it is placed in input 220). A STAT sample can enter the track 200 immediately after being placed at input 222 or, if track 200 is overcrowded, the STAT sample can enter the track at the next available uncrowded operation cycle. Some embodiments monitor the number of carriers on the track during an operation cycle and limit the total number to a manageable amount, leaving the remainder in input queues. By restricting samples at the input, track 200 can be free of traffic, allowing it to always be operated in the most efficient manner possible. In these embodiments, the transit time of a sample between two modules can be a bounded value (e.g., less than some portion of an operation cycle), allowing simplified scheduling.

In some embodiments, the track system 200 can be designed to be bidirectional. This means that sample carriers can traverse the outside path and/or any sub-paths in either direction. In some embodiments, additional sub-paths, such as 211B accessed via additional decision points 215 and 217, can assist in providing bidirectional access. Bidirectional paths can have inherent advantages. For example, if normal priority samples are always handled in the same direction, a STAT sample can be handled in the opposite direction along the sub-path. This means that a STAT sample can essentially enter the exit of the sub-path and be immediately placed at the head of the queue without requiring the queue to be flushed. For example, if a STAT sample is placed on track 200 at segment 204, it can enter path 210B via decision point 214 and proceed into path 210B to be immediately placed at the head of any queue. Meanwhile, in all of these examples, because queues are presumed to be limited generally to sub-paths, there is no need to flush queues in other modules if a STAT sample does not need immediate access to those modules. Any additional modules that need to service a STAT sample on a subsequent cycle can flush their queues at that point, providing just-in-time access to a STAT sample without otherwise disrupting the operation of each analyzer module.

Modular design also allows certain other advantages. If the automation systems within an analyzer module are adapted to take advantage of the track system contained in the module, new features can be added that use the common track. For example, a module could have its own internal reagent carousel that includes all of the reagents necessary for performing the assays prescribed for the samples. When reagents stocked in the analyzer module run low, an operator can replenish the reagents in some embodiments by simply loading additional reagents onto carriers on the track 200. When the reagents on track 200 reach the appropriate module, the module can utilize mechanical systems such as an arm or a feeder system that takes the reagents off of the track and places the reagents in the reagents store for the module.

In some embodiments, the individual track portions shown in FIG. 5 and FIG. 4A and FIG. 4B can be operated independently from one another, or can be passive. Independent carrier movement provides advantages over friction-based track systems, such as non-localized conveyor belts where the entire friction track must be moved to effect movement of a sample carrier. This means that other samples also on that track must move at the same rate. This also means that if certain sections operate at different speeds, collisions between passive carriers carrying samples can occur.

FIG. 6A depicts an exemplary carrier 250 for use with the present invention. Carrier 250 can hold different payloads in different embodiments. One payload can be a sample tube 255, which contains a fluid sample 256, such as blood or urine. Other payloads may include racks of tubes or reagent cartridges or any other suitable cartridge. Sample carrier 250 includes a main body 260, which can house the internal electronic components describe herein. The main body 260 supports a bracket 262, which can accept a payload. In some embodiments, this is a shallow hole that is designed to accept a fluid container 255, such as a sample tube, and hold it with a friction fit. In some embodiments, the friction fit can be made using an elastic bore or a clamp that can be fixed or energized with a spring to create a holding force. In some embodiments, sample racks and reagent cartridges can be designed to also attach to the bracket 262, allowing bracket 262 to act as a universal base for multiple payload types.

Body 260 can include or be coupled to guide portion 266, which allows the carrier 250 to follow a track between decision points. Guide portion 266 can include, for example, a slot to accept one or more rails in the track, providing lateral and/or vertical support. In some embodiments, the guide portion allows the carrier 250 to be guided by walls in the track, such as the walls of a trough-shaped track. The guide portion 266 can also include drive mechanisms, such as friction wheels that allow a motor in the carrier body 260 to drive the carrier or puck 250 forward or backward on the track. The guide portion 266 can include other drive components suitable for use with the embodiments described throughout, such as magnets or induction coils.

Rewritable display 268 can be provided on the top of the carrier 250. This display can include an LCD oriented panel and can be updated in real time by the carrier 250 to display status information about sample 256. By providing the electronically rewritable display on the top of the carrier 250, the status information can be viewed at a glance by an operator. This can allow an operator to quickly determine which sample he/she is looking for when there are multiple carriers 250 in a group. By placing the rewritable display on top of the carrier 250, an operator can determine status information even when multiple carriers 250 are in a drawer or rack.

Figure 6B:
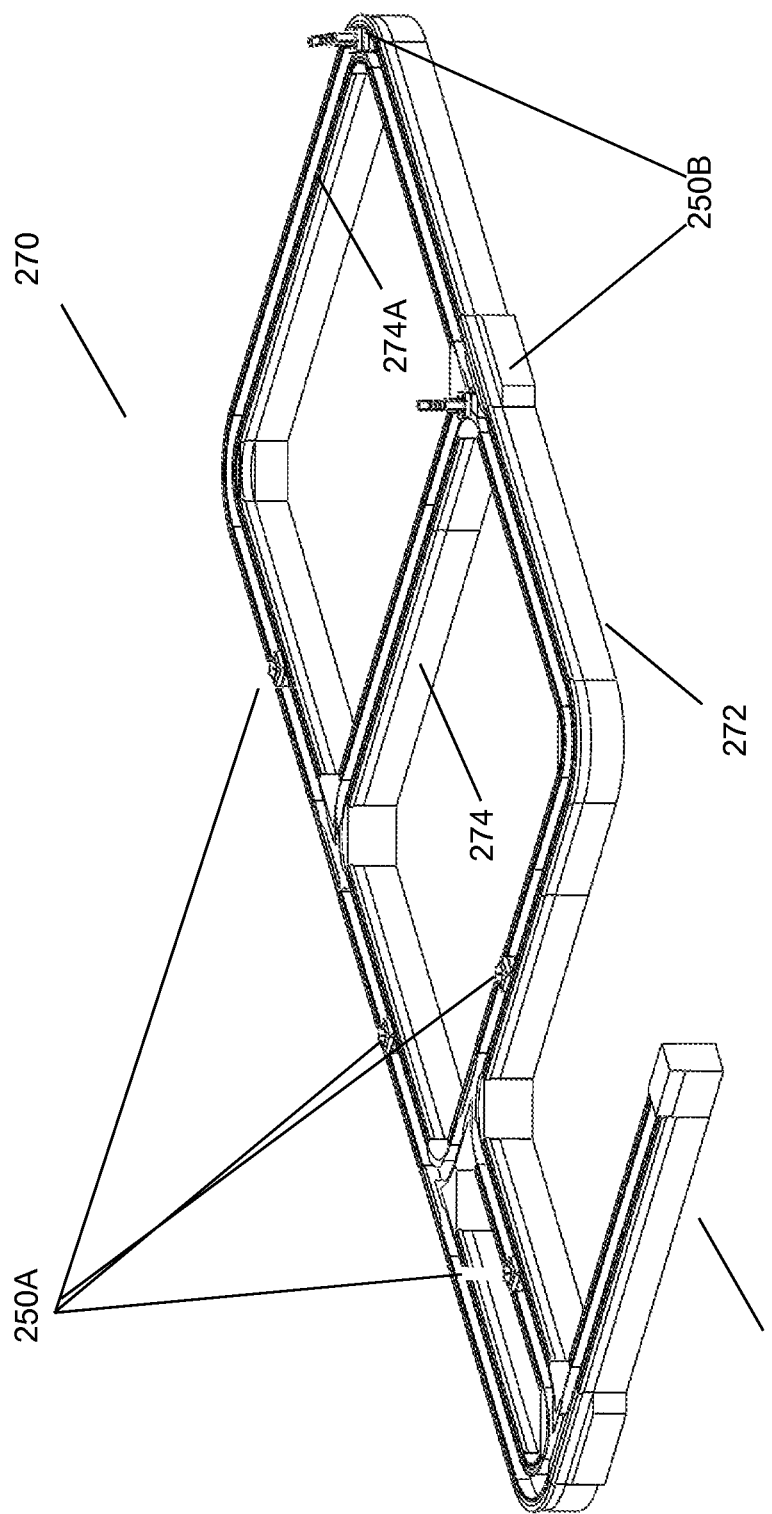
FIG. 6B is a perspective view of an exemplary track configuration that can be used with the embodiments disclosed herein.

FIG. 6B shows an exemplary track configuration 270 for use by carriers 250. In this example, carriers 250A transport sample tubes, while carriers 250B transport racks of tubes along main track 272 and/or subpaths 274 and 274A. Path 276 can be used by an operator to place samples into carriers or remove samples from these carriers.

Figure 6C:
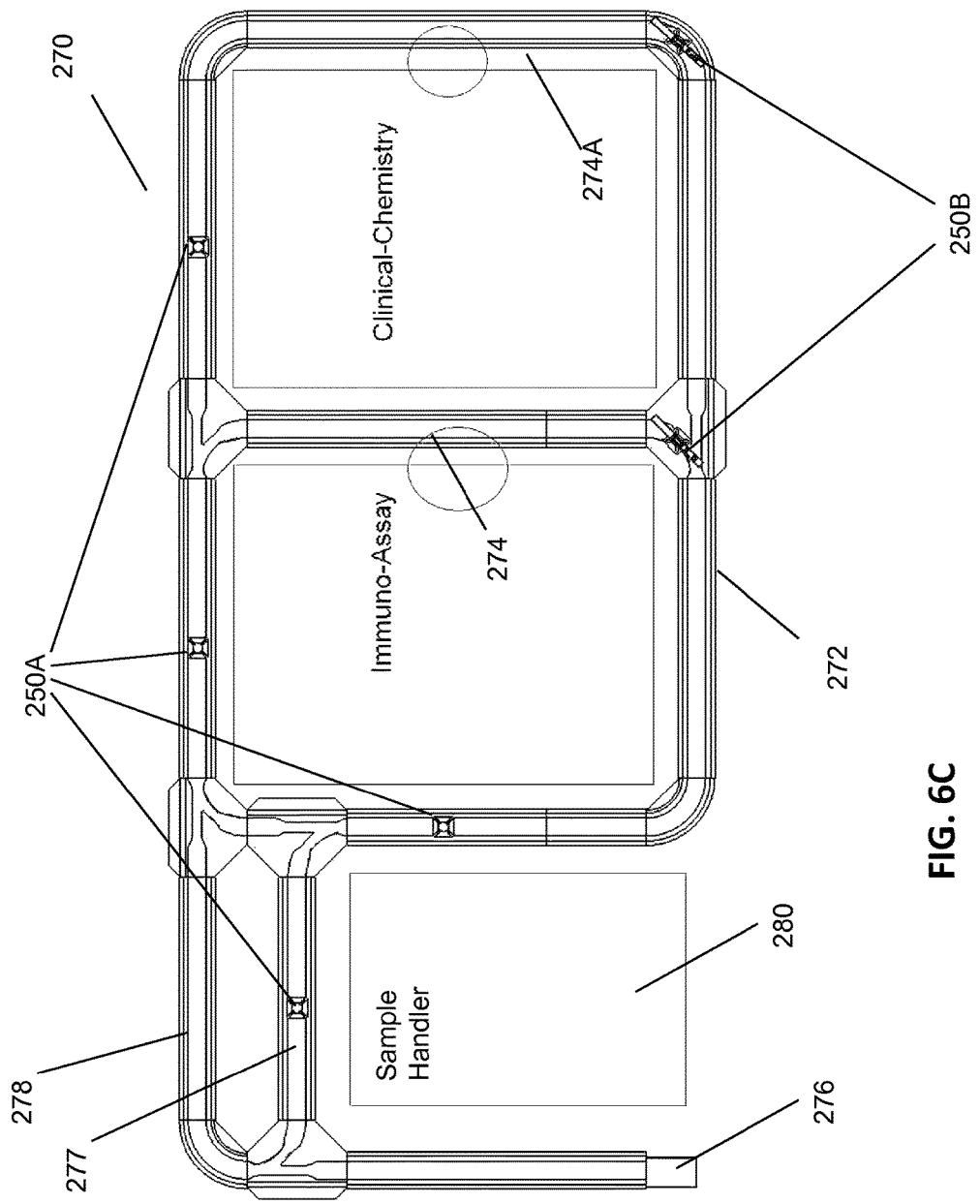
FIG. 6C is a top view of an exemplary automation systems that can be used with the embodiments disclosed herein.

FIG. 6C shows an additional view of an exemplary track configuration 270. In this example, sub-path 274 serves an immunoassay station, while sub-path 274A serves a clinical chemistry station. Input/output lane 276 can be served by a sample handler station 280 that uses sub paths 277 and 278 to buffer samples for insertion or removal of the samples from the main track 272.

In some embodiments, the sample handler 280 can also load and unload samples or other payloads to/from the carriers 250A and 250B. This allows the number of carriers to be reduced to the amount needed to support payloads that are currently being used by the stations in track system 270, rather than having a vast majority of carriers sitting idle on tracks 277 and 278 during peak demand for the analyzer. Instead, sample trays (without the carriers disclosed herein) can be placed/removed by an operator at input/output lane 276. This can reduce the overall cost of the system and the number of carriers needed can be determined by the throughput of the analyzer, rather than based on anticipating the peak demand for the analyzer in excess of throughput.

Intelligent Carriers

Some embodiments of the present invention can utilize intelligent independent carriers to enable certain improvements over passive pucks on friction-based tracks. For example, one disadvantage of prior art track systems is that at each decision point the decision for directing a puck is made by the track by rotating the puck and reading a barcode optically. Rotating and optical reading is a relatively slow process. Furthermore, this process can be redundant because the system has knowledge of the identification of the sample tube when the sample tube is placed into the puck by an operator. Embodiments of the present invention can include carriers that have means to identify the contents of the sample tube (and optionally communicate this information to the automation system) without requiring the carrier to be stopped, rotated, and read optically.

For example, a carrier can include an onboard optical reader to automatically read a barcode of a payload. The results of the scan can then be stored in the memory of a carrier if the carrier has onboard processing capability. Alternatively, an outside source, such as a hand barcode reader operated by an operator at the time of placing the sample into the carrier, can communicate the barcode information of the payload to the carrier via RF signal or other known means, such as communication protocol using temporary electrical contact or optical communication. In some embodiments, the association of the carrier with the payload can be stored external to the carrier and the identity of the carrier can be conveyed by the carrier to the system by RF, optical, or near field communication, allowing the system to assist in routing or tracking the carrier and the payload. Routing decisions can then be made by the carrier or by identifying the carrier, rather than reading a unique barcode of a payload.

By moving processing capability and/or sensor capability onto each individual carrier, the carriers can participate actively and intelligently in their own routing through the track system. For example, if individual carriers can move independently of one another either by autonomous motive capabilities or by communication with the track, certain performance advantages can be realized.

By allowing carriers to move independently, carriers can move around the track faster. One key limitation on the motion of a carrier is that it should not spill an open-tube sample. The limiting factor is generally not the velocity of the carrier in a straight line, but the acceleration and jerk experienced by the carrier (while speeding up, slowing down, or turning), which may cause splashing. For prior-art friction-based track systems, the velocity of the track is typically limited to prevent acceleration and jerk experienced by pucks from exceeding threshold amounts because the entire track moves. However, by using a track system with independently operating sections that can respond to individual carriers, or individual carriers that have independent motive capability, the acceleration of any given carrier can be tailored to limit acceleration/deceleration and jerk, while allowing the average velocity to be greater than that of traditional tracks. By not limiting the top speed of a carrier, the carrier can continue to accelerate on each track section as appropriate, resulting in a substantially higher average speed around the track. This can assist the carrier in traversing the entire track system in less than one machine cycle of the analyzer. These machine cycles can be, for instance 20 or 40 seconds.

Similarly, an autonomous carrier can know its own identity and that of its payload. This allows the carrier to actively participate or assist in the routing decision process at individual decision points. For example, upon reaching a decision point (e.g., switch, intersection, junction, fork, etc.), a carrier can communicate its identity and/or the identity of its payload to the track or any switching mechanism (or its intended route that the carrier has determined based on the payload identity), via RF or near field communication. In this scenario, the carrier does not need to be stopped at a decision point for a barcode scan. Instead, the carrier can keep going, possibly without even slowing down, and the carrier can be routed in real time. Furthermore, if the carrier knows where it is going or communicates its identity to the track (such that the track knows where the carrier is going) before the carrier physically reaches a decision point, the carrier can be made to decelerate prior to a decision point if the carrier will be turning. On the other hand, if the carrier does not need to turn at the decision point, the carrier can continue at a higher velocity because the sample carried by the carrier will not undergo cornering forces if the carrier is not turning at the decision point or a curved section of the track.

An autonomous carrier can also include onboard processing and sensor capabilities. This can allow a carrier to determine where it is on the track and where it needs to go, rather than being directed by the track (although in some embodiments, a central controller sends routing instructions to the carrier to be carried out). For example, position encoding or markers in the track can be read by the carrier to determine a carrier's location. Absolute position information can be encoded on a track surface to provide reference points to a carrier as it traverses the track. This position encoding can take many forms. The track may be encoded with optical markers that indicate the current section of the track (e.g., like virtual highway signs), or may further include optical encoding of the specific absolute location within that section of track (e.g., like virtual mile markers). Position information can also be encoded with markings between absolute position marks. These can provide synchronization information to assist a carrier in reckoning its current trajectory. The optical encoding scheme may take on any appropriate form known to one skilled in the art. These marks used by the encoding scheme may include binary position encoding, like that found in a rotary encoder, optical landmarks, such as LEDs placed in the track at certain positions, barcodes, QR codes, data matrices, reflective landmarks, or the like. General position information can also be conveyed to the carrier via RF/wireless means. For example, RFID markers in the track can provide near field communication to the carrier to alert the carrier that it has entered a given part of the track. In some embodiments, local transmitters around or near the track can provide GPS-like positioning information to enable the carrier to determine its location. Alternatively, sensors in the track, such as Hall effect sensors or cameras, can determine the position of individual carriers and relay this information to the carrier.

Similarly, the carrier can have sensors that indicate relative motion, which provide data that can be accumulated to determine a position. For example, the carrier may have gyroscopes, accelerometers, or optical sensors that observe speckle patterns as the carrier moves to determine velocity or acceleration, which can be used to extrapolate a relative position.

Because a carrier can know where it is and its motion relative to the track, a carrier can essentially drive itself, provided it knows its destination. The routing of the carrier can be provided in many different ways in various embodiments. In some embodiments, when a carrier is loaded with the sample, the system can tell the carrier the destination analyzer station. This information can be as simple as the identification of the destination station in embodiments where the carrier has autonomous routing capability. This information can also be detailed information such as a routing list that identifies the specific path of the individual track sections and decision points that a carrier will traverse. Routing information can be conveyed to the carrier via any communication method described herein, such as RF communication, near field/inductive communication, electrical contact communication, or optical communication.

In an exemplary embodiment, when an operator scans the barcode of the sample tube and places it in a carrier, the system determines the identity of the carrier and matches it with the identity of the sample. The system then locates the record for the sample to determine which tests the sample must undergo in the analyzer. A scheduler then allocates testing resources to the sample, including choosing which tests will be done by individual testing stations and when the sample should arrive at each testing station for analysis. The system can then communicate this schedule (or part of the schedule) to the carrier to inform the carrier of where it needs to go, and optionally when it needs to go and/or when it needs to arrive.

Once the carrier is placed onto the track system, the routing capabilities and location acquisition systems of the carrier enable the carrier to determine where it is on the track and where it needs to go on the track. As the carrier traverses the track, the carrier reaches individual decision points and can be directed along the main track or along sub-paths as appropriate. Because each carrier operates independently from one another, a carrier can do this quite quickly without necessarily stopping at each decision point and without waiting for other carriers in a queue. Because these carriers move quickly, there is less traffic on the main sections of the track, which reduces the risk of collision or traffic jams at decision points or corners in the track (e.g., sections where carriers might slow down to avoid excessive forces on the sample).

Motive force can be provided to the carriers in many ways. In some embodiments, the track actively participates in providing individualized motive force to each carrier. In some embodiments, motive force is provided by electromagnetic coils in the track that propel one or more magnets in the carrier. An exemplary system for providing this motive force is the track system provided by MagneMotion, Inc., which can generally be understood by the description of the linear synchronous motors (LSMs) found in US Published Patent Application 2010/0236445, assigned to MagneMotion, Inc. These traditional systems utilizing this magnetic motion system have included passive carriers that lack the integrated intelligence of the carriers described herein, and all routing and decisions are made by a central controller with no need for active carriers that participate in the routing and identification process.

In embodiments that utilize magnetic motion, the electromagnetic coils and the magnets operate as an LSM to propel each individual carrier in the direction chosen with precise control of velocity, acceleration, and jerk. Where each coil on the track (or a local set of coils) can be operated independently, this allows highly localized motive force to individual carriers such that individual carriers can move with their own individually tailored accelerations and velocities. Coils local to a carrier at any given moment can be activated to provide precise control of the direction, velocity, acceleration, and jerk of an individual carrier that passes in the vicinity of the coils.

In some embodiments, a track may be comprised of many individually articulable rollers that act as a locally customizable friction track. Because individual micro-sections of the track can be managed independently, rollers immediately around a carrier may be controlled to provide individualized velocity, acceleration, and jerk. In some embodiments, other active track configurations can be used that provide localized individual motive force to each carrier.

In some embodiments, the track may be largely passive, providing a floor, walls, rails, or any other appropriate limitations on the motion of a carrier to guide the carrier along a single dimension. In these embodiments, the motive force is provided by the carrier itself. In some embodiments, each individual carrier has one or more onboard motors that drive wheels to provide self-propelled friction-based motive force between the track and the carrier. Unlike traditional friction tracks, where the track is a conveyor, carriers with driven wheels can traverse the track independently and accelerate/decelerate individually. This allows each carrier to control its velocity, acceleration, and jerk at any given moment to control the forces exerted on its payload, as well as traverse the track along individually tailored routes. In some embodiments, permanent magnets may be provided in the track and electromagnets in the carrier may be operated to propel the carrier forward, thereby acting as an LSM with the carrier providing the driving magnetic force. Other passive track configurations are also contemplated, such as a fluid track that allows carriers to float and move autonomously via water jets or the like, a low friction track that allows carriers to float on pockets of air provided by the track, (e.g., acting like a localized air hockey table), or any other configuration that allows individual carriers to experience individualized motive forces as they traverse the track.

Figure 7:
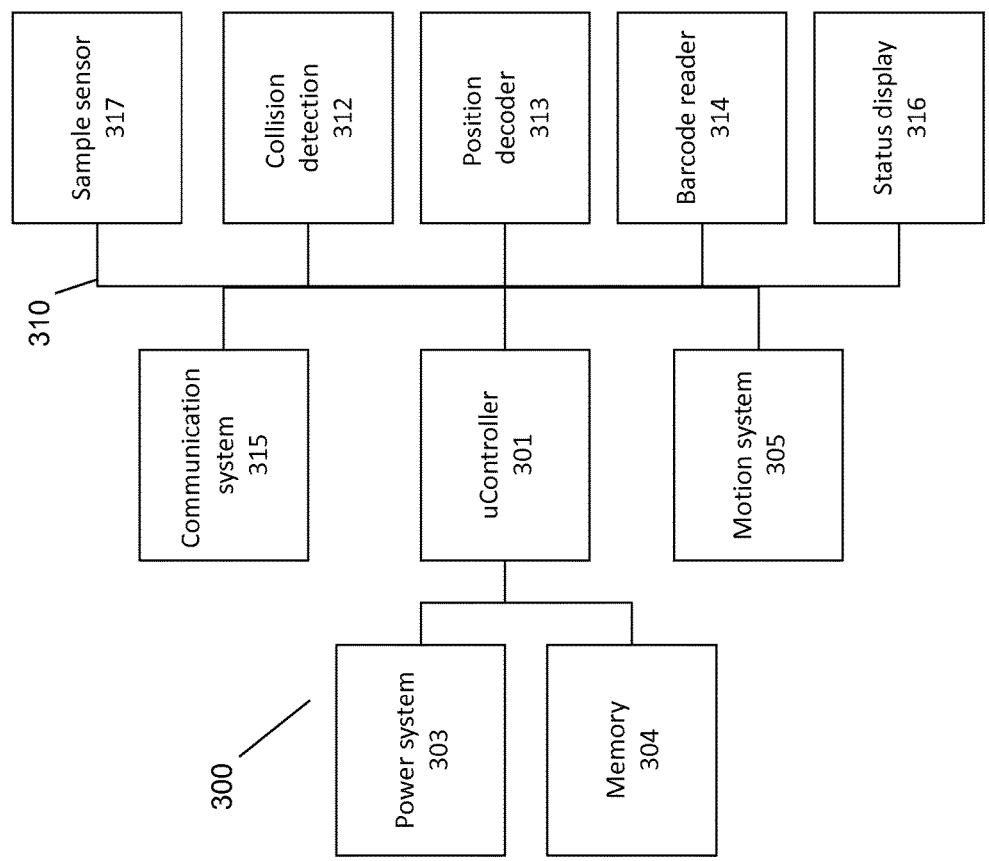
FIG. 7 is a system block diagram of the control systems including onboard active carriers that can be used with certain embodiments disclosed herein.

FIG. 7 shows a top-level system diagram of the control systems and sensors for an exemplary intelligent autonomous carrier 300. Carrier 300 is controlled by a microcontroller 301 that includes sufficient processing power to handle navigation, maintenance, motion, and sensor activities needed to operate the carrier. Because the carrier is active and includes onboard electronics, unlike prior art passive carriers, the carrier includes an onboard power station. The details of this station vary in different embodiments of the present invention. In some embodiments, power system 303 comprises a battery that may be charged as the carrier operates, while in other embodiments, the battery is replaceable or can be manually charged when the carrier is not operating. Power system 303 can include the necessary charging electronics to maintain a battery. In other embodiments, power system 303 comprises a capacitor that may be charged by inductive or electrical contact mechanisms to obtain electrical potential from the track itself, in much the same way a subway car or model train might receive power.

Microcontroller 301 communicates with system memory 304. System memory 304 may include data and instruction memory. Instruction memory in memory 304 includes sufficient programs, applications, or instructions to operate the carrier. This may include navigation procedures as well as sensor handling applications. Data memory in memory 304 can include data about the current position, speed, acceleration, payload contents, navigational plan, identity of the carrier or payload, or other status information. By including onboard memory in carrier 300, the carrier can keep track of its current status and uses information to intelligently route around the track or convey status information to the track or other carriers.

Microcontroller 301 is responsible for operating the motion system 305, sensors 312, 313, and 314, communication system 315, status display 316, and sample sensor 317. These peripherals can be operated by the microcontroller 301 via a bus 310. Bus 310 can be any standard bus, such as a CAN bus, that is capable of communicating with the plurality of peripherals, or can include individual signal paths to individual peripherals. Peripherals can utilize their own power sources or the common power system 303.

Motion system 305 can include the control logic necessary for operating any of the motion systems described herein. For example, motion system 305 can include motor controllers in embodiments that use driven wheels. In other embodiments, motion system 305 can include the necessary logic to communicate with any active track systems necessary to provide a motive force to the carrier 300. In these embodiments, motion system 305 may be a software component executed by microcontroller 301 and utilizing communication system 315 to communicate with the track. Devices such as motors, actuators, electromagnets, and the like, that are controlled by motion system 305 can be powered by power system 303 in embodiments where these devices are onboard the carrier. External power sources can also provide power in some embodiments, such as embodiments where an LSM provides motive force by energizing coils in the track. In some embodiments, motion system 305 controls devices on or off the carrier to provide motive force. In some embodiments, the motion system 305 works with other controllers, such as controllers in the track, to coordinate motive forces, such as by requestingnearby coils in the track be energized or requesting the movement of local rollers. In these embodiments, motion system 305 can work together with communication system 315 to move the carrier.

Carrier 300 can include one or more sensors. In some embodiments, carrier 300 includes a collision detection system 312. Collision detection system 312 can include sensors at the front or back of a carrier for determining if it is getting close to another carrier. Exemplary collision detection sensors can include IR range-finding, magnetic sensors, microwave sensors, or optical detectors. Whereas many prior art pucks are round, carrier 300 may be directional, having a front portion and a rear portion. By having a directional geometry, carrier 300 can include a front collision detector and a rear collision detector.

In some embodiments, collision detection information can include information received via the communication system 315. For example, in some embodiments, the central controller for the track can observe the location and speed of carriers on the track and evaluate collision conditions and send updated directions to a carrier to prevent a collision. In some embodiments, nearby carriers can communicate their positions in a peer-to-peer manner. This allows carriers to individually assess the risk of collision based on real-time position information received from other carriers. It will be understood that in embodiments where the carrier receives trajectory information about other carriers, or decisions are made with the help of a centralized controller that has access to trajectory information of nearby carriers, the carriers need not be directional, and can include sensors or receivers that do not depend on a given orientation of a carrier.

Carrier 300 can also include a position decoder 313. This sensor can extrapolate the carrier's position as described herein. For example, position decoder 313 can include a camera or other optical means to identify landmarks in the track, or observe optical encoding in the track. In some embodiments, position decoder 313 can also include inertial sensors, magnetic sensors, or other sensors sufficient to determine a carrier's current position, direction, velocity, acceleration, and/or jerk.

Carrier 300 can optionally include a barcode reader 314. If equipped with barcode reader 314, carrier 300 can observe the barcode of its payload at the time the samples are loaded onto the carrier or at any time thereafter. This prevents the need for a carrier to stop at individual decision points to have the system read the barcode of a sample tube. By reading and storing the identity of the sample tube, or conveying this information to the overall system, a carrier may more efficiently traverse the track system because routing decisions can be made in advance of reaching a decision point. Alternatively, where a system knows the identity of the sample when it is placed onto the carrier, the system can include an external barcode reader and can convey the identity of the payload to the carrier for storage and memory 304 via communication system 315.

Communication system 315 can comprise any mechanisms sufficient to allow the carrier to communicate with the overall automation system. For example, this can include an XBee communication system for wireless communication using an off-the-shelf communication protocol, such as 802.15.4, any appropriate version of 802.11, or any standard or proprietary wireless protocol. Communication system 315 can include a transceiver and antenna and logic for operating an RF communication protocol. In some embodiments, communication system 315 can also include near field communication, optical communication or electrical contact components. Information conveyed via the communications system to/from carrier 300 is described throughout this application.

In some embodiments, the carrier can also include a status display module 316. The status display module 316 can include a controller and rewritable electronic display, such as an LCD panel or E-ink display. In some embodiments, the controller is treated as an addressable portion of memory, such that the microcontroller 301 can easily update the status display 316.

In some embodiments, the carrier also includes sample sensor 317. This sensor can be used to indicate the presence or absence of a fluid container in the carrier's tube bracket (which may also be referred to as a tube holder). In some embodiments, this is a momentary mechanical switch that is depressed by the presence of a tube and not depressed when a tube is absent. This information can be used to determine the status of a tube, which can assist in the display of status information by status display module 316.

Routing

The desire for rapid transit times within an analyzer system can make routing difficult. In prior art systems, rapid routing is less critical because samples are generally stopped, singulated, and scanned at each decision point. In those systems, the routing decision for a given decision point can be made while the sample is stopped. Rapid routing decisions are generally desired, and may require determining a switching decision before a sample carrier reaches a decision point. Furthermore, because the carriers move at a rapid rate compared to the prior art, the control of the instantaneous trajectory of a sample carrier can be assisted by real-time processing in order to prevent spilling or damaging IVD samples. In some embodiments, substantially instantaneous trajectory observation and control is conducted on-board each carrier to facilitate real-time control, while the overall routing decisions are made by a central controller that manages a group of carriers. Therefore, in some embodiments of the present invention, the carriers act like semi-autonomous robots that receive global routing instructions from a central controller, but make local motion decisions substantially autonomously.

For example, when a carrier receives a sample (e.g., a patient fluid sample or other payload) a central controller managing one or more carriers determines the schedule for that carrier and instructs the carrier where to go on the track of, for example, an in vitro diagnostics automation system. This instruction can be a next-hop instruction (e.g., identifying the next leg of a route), such as going to a given decision point, moving forward to the next decision point, or turning at a given decision point. In some embodiments, the instructions can include a complete or partial list of track segments and decision points to be traversed and whether to turn at each decision point. These instructions can be communicated to the carrier from a central controller via any conventional means, including wireless or contact electrical signaling, as explained throughout this disclosure.

While following the instructions, each carrier can make a determination of the appropriate velocity, acceleration, and jerk (as used herein, acceleration includes deceleration). This can include a real-time decision of whether the carrier must slow down to avoid collision or to enter a curve without causing excessive lateral forces, or slow down before the next decision point. These decisions can be made with the assistance of any on-board sensors, as well as external information received by the carrier, such as information about the position and trajectory of nearby carriers. For example, accelerometers and/or track encoding information can be used to determine the current velocity, acceleration, and jerk, as well as the current position of a carrier. This information can be used by each carrier to determine its trajectory and/or can be conveyed to other carriers. Collision detectors, such as RF rangefinders, can determine whether or not a potential collision condition exists to assist the carrier in determining whether it needs to slow down and/or stop. This collision determination can include trajectory information about the current carrier, as well as the trajectory information about surrounding carriers received by the current carrier through observation or by receiving information from a central scheduler for the track.

Figure 8:
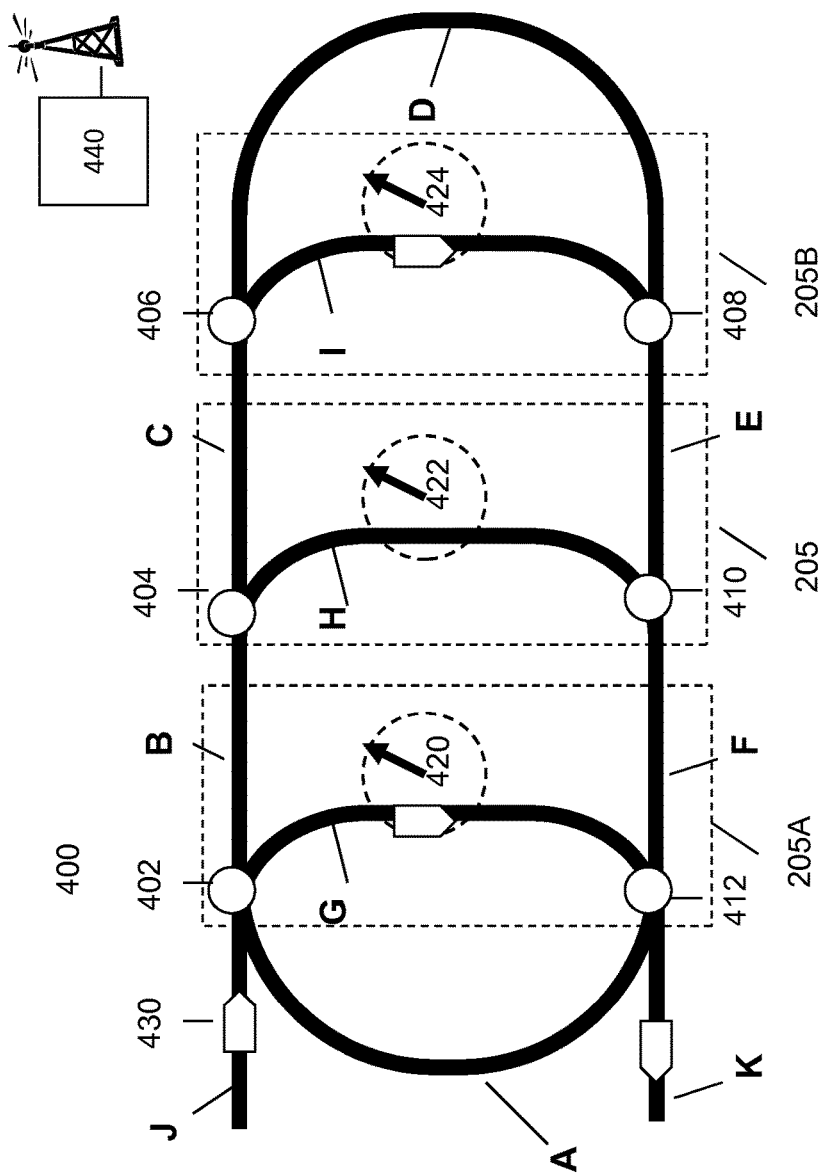
FIG. 8 is a diagrammatic view of exemplary routes in an exemplary track configuration that can be used for navigation of sample carriers in certain embodiments.

FIG. 8 shows an exemplary routing scenario in automation system 400. Carrier 430 receives routing instructions from central management processor 440 via RF signaling. Central management processor 440 can participate in monitoring and directing carriers, including issuing routing instructions and scheduling the movement and dispatch of carriers. Central management processor 440 can be part of the central controller and/or local controllers that interact with individual modules or situations. Central or local controllers can also act at the direction of central management processor 440. Central management processor 440 can include one or more processors operating together, independently, and/or in communication with one another. Central management processor 440 can be microprocessor, software operating on one or more processors, or other conventional computer means suitable for calculating the schedule for multiple carriers within the track system 400.

Central management processor 440 can receive position information from multiple carriers, as well as any sensor information from sensors in the track system 400 and/or information reported by the carriers. Central management processor 440 uses the status information of the carriers and track as well as the identity of samples or other payload carried by the carriers and the required assays to be performed by the system on these samples.

The exemplary track 400 shown in FIG. 8 includes a first curve segment A, that connects to straight segment B and a pullout segment G (e.g., a segment that serves a testing station), which serves analyzer/testing station 205A and pipette 420, via decision point 402. Segment B connects to straight segment C and a pullout segment H, which serves analyzer/testing station 205 and pipette 422, via decision point 404. Segment C connects to curved segment D, which serves sample handling station 205C, and pullout segment I, which serves analyzer/testing station 205B and pipette 424, via decision point 406. Segment D connects to straight segment E and the other end of pullout segment I, via decision point 408. That is, there are different paths between decision points 406 and 408—segments D and I, (where segment I is a pullout that can be used to deliver samples to interact with pipette 424). Segment E connects to straight segment F and the other end of pullout segment H, via decision point 410. Segment F connects to curved segment A and the other end of pullout segment G, via decision point 412. In some embodiments, track 400 includes input and output lanes J and K, which can be used to add or remove carriers at decision points 402 and 412.

In some embodiments, decision points 402-412 are passive forks in the track that carrier 430 can navigate to select a proper destination segment. In other embodiments, decision points 402-412 are active forks that can be controlled by carrier 430 or central management processor 440. In some embodiments, decision points 402-412 are electromagnetically controlled switches that respond to requests by carrier 430, such as via RF or near field communication. In some embodiments these electromagnetically controlled switches have a default position, such as straight, that the switch will return to once a carrier has been routed. By using default positions for decision points, a carrier may not need to request a position at each decision point, unless it needs to be switched at that decision point.

Scheduler central management processor 440 assigns carrier 430 a first route, Route 1, to place the carrier 430 and its payload within reach of pipette 420. Carrier 430 is instructed to travel along segment J to decision point 402 and travel onto segment G to stop at a position accessible to pipette 420. In some embodiments, carrier 430 receives the instructions and determines its current location and trajectory to determine a direction and trajectory to use to reach decision point 402. Carrier 430 can also take into account that it will be making a hard right turn at decision point 402 onto segment G. In some embodiments, decision point 402 includes a switching mechanism in the track that can operate under the control of carrier 430. In these embodiments, carrier 430 communicates with the track on approach to decision point 402 to request switching onto segment G. In other embodiments, carrier 430 may have a steering mechanism (such as moveable guide wheel, directional magnets, asymmetric brakes, or the like) that allows carrier 430 to make a right turn onto segment G at decision point 402, without the assistance of an external gate integrated into the track. In these embodiments, carrier 430 engages the steering mechanism at decision point 402 to make the turn onto segment G.

Carrier 430 can determine its rough location—its current track section, such as section J, by reading encoding in the track, such as optical encoding, or RFID tags. In some embodiments, carrier 430 uses multiple means to determine its location within the track system 400. For example, RFID tags can be used to determine generally on which track segment the carrier 430 is located, while optical encoding or other precise encoding can be used to determine the position within that track segment. This encoding can also be used to determine velocity, acceleration, or jerk by observing changes in the encoding (e.g., derivatives from the position information).

Carrier 430 can use the identification of the current track section to determine the appropriate route to the destination section either by explicit instruction received by the central management processor 440 or by looking up an appropriate route in an onboard database in memory 304, as shown in the onboard control systems in FIG. 7. In some embodiments, the carrier 430 has an understanding of how to reach section G from section J based on a map stored in the memory of carrier 430 in memory 304. This map can include a simple lookup table or a tree of track sections where each node is linked by the corresponding decision points, or vice versa.

For example, upon identifying that the carrier is currently in the track section J, the onboard database can inform carrier 430 to proceed to decision point 402 to be switched to the right onto section G.

As shown in FIG. 8, carrier 430 responds to instructions for Route 1 by proceeding onto section G and stopping at a position near pipette 420. Once the carrier 430 is stopped, it can receive additional instructions from the analyzer/testing station controlling pipette 420. For example, analyzer 205A can control pipette 420 and can instruct carriers on section G to position themselves at precise points along section G. This allows analyzer/testing stations to treat track sections as random-access queues. For example, once carrier 430 stops on section G, additional instructions can be conveyed via central management processor 440 or directly from analyzer 205A to the carrier 430 via RF transmission or other means, such as local optical or inductive/near field signals. These instructions can include halting while another carrier interacts with pipette 420, and subsequently proceeding to a position accessible to pipette 420, when analyzer 205A is ready to perform one or more assays on the sample carried by carrier 430.

Once analyzer/testing station 205A has finished interacting with the sample carried by carrier 430, additional routing instructions can be sent to the carrier 430 from the central management processor 440. For example, Route 2 can include routing instructions to proceed to section H to interact with pipette 422. In some embodiments, the routing tables contained within onboard memory 304 of carrier 430 have sufficient information about the track layout to allow the carrier to route itself to section H. In other embodiments, a list of routing steps can be transmitted to carrier 430 via central management processor 440. It will be appreciated that other embodiments can include conveying any subset of the route to carrier 430 and/or sending routing instructions in a piecemeal fashion, such that carrier 430 always knows the next routing step, and optionally subsequent routing steps.

In this example, carrier 430 receives a route list representing Route 2 from central management processor 440 instructing it to proceed via section G to decision point 412. At decision point 412, carrier 430 will initiate switching onto section A by interacting with a gate or by turning as described above. Carrier 430 can take into account curved track conditions on section G and section A to ensure that acceleration and jerk conditions do not exceed a threshold requirement for the sample it carries. This can prevent spillage or instability during transit. The route information received by carrier 430 then instructs carrier 430 to proceed through decision point 402 without turning. The trajectory used in Route 2 when approaching decision point 402 can be different (e.g., faster) from that used during Route 1, because carrier 430 knows that it does not need to make a sharp right turn onto section G. In some embodiments, this allows carrier 430 to approach decision point 402 with a substantially greater velocity during Route 2 than during Route 1. By traversing decision point 402 faster if carrier 430 is not turning, carrier 430 can complete Route 2 in less time than embodiments in which carrier 430 must slow down for possible switching at each decision point. This is an improvement over the prior art, where carriers are typically halted and singulated, regardless of whether the carrier is turning or not.

After passing decision point 402, carrier 430 proceeds onto section B. At decision point 404, carrier 430 proceeds to section C. At decision point 406, carrier 430 prepares and turns onto section I, where it stops for interaction with pipette 424. Like section G, section I can act as a queue for pipette 424 and carrier 430 can be controlled under local instruction by the analyzer/testing station 205B served by section I.

When pipette 424 is done interacting with carrier 430, central management processor 440 can provide new routing instructions to carrier 430 instructing carrier 430 to proceed onto an output path K. Route 3 can be handled in the same manner as Route 1 and Route 2. Upon receiving instructions for Route 3, carrier 430 proceeds down section I to decision point 408 where it turns back onto a main track section E and proceeds past decision point 410, track section F, and decision point 412 (without needing to slow down in some embodiments), and onto section K where the carrier 430 and/or the sample can be removed from the system by an operator. Carrier 430 can then be reused for samples at input section J. Upon receiving instructions for Route 4, carrier 430 proceeds down section D to sample handling station 205C and to decision point 408 where it turns back onto a main track section E and then proceeds the same as Route 3.

In some embodiments, each track section of FIG. 8 can be configured to include one or more speed zones. This may be represented as a speed or acceleration limit in software that maintains motion profiles for each carrier. For example, section D may be represented for trajectory control as a slow speed zone for all carriers to account for the inherent centripetal forces exerted by the track as carriers traverse section D. Similarly, track sections can include multiple speed zones within the track section, which may include motion profile rules. For example, a carrier may slow down responsive to software enforcement of rules that identify the latter portion of section C as a braking zone due to the upcoming speed limited zone in track section D. In some embodiments, software responsible for maintaining motion profile rules for carriers may take into account an upcoming speed zone and brake in an unlimited track section in anticipation. Furthermore, different track section portions can be represented as dynamic speed zones. For example, a stopping point for interaction with a pipette can be represented a speed zone with a speed of zero for carriers that should stop at that location. This may allow trajectory enforcing software to automatically slow down the affected carrier as it approaches the stopping position.

Figure 9:
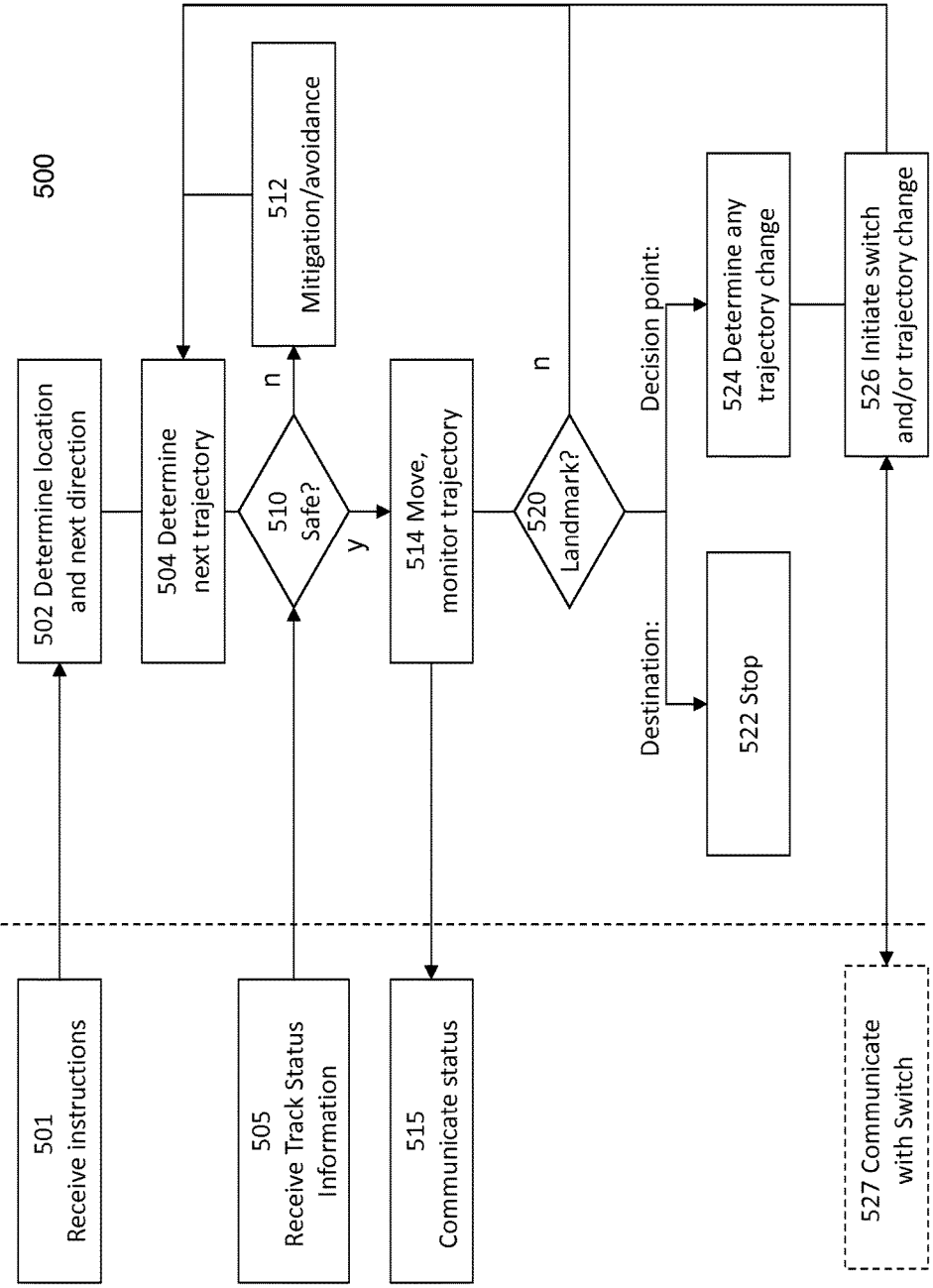
FIG. 9 is a flow diagram showing the operation of the navigation of sample carriers in certain embodiments.

FIG. 9 shows a general operational diagram of carrier 430 as it follows routing instructions. As can be seen in method 500, the actions can be taken by the carrier with minimal control by, or interaction with, a central scheduler, such as a central management controller. At step 501 the carrier receives routing instructions from, for example, a central scheduler. In this example, the routing instructions include enough information for the carrier to determine its entire route to a destination point in the track system. These instructions can include a list of all routing points, including decision points to turn at and sections to traverse. In some embodiments, routing instructions can include the destination point and onboard routing information can be used by the carrier to determine the best route to take. It will be appreciated that, when at least a main track is unidirectional, the routing calculation by the carrier is fairly simple and can comprise any known method including searching a tree of nodes and sections or searching a lookup table of possible route permutations.

These instructions can also include velocity and acceleration motion profiles for each section. In some embodiments, velocity and acceleration for each section of track can be calculated by the carrier based on its payload and based on information in an onboard database, such as length of track, curvature of track, location of decision points, the type of sample or payload being carried, and consideration of whether the carrier will turn or proceed in the same direction upon reaching a decision point. In some embodiments, the routing information received at step 501 also includes timing information to instruct the carrier when to begin transit and/or when to complete transit.

Upon receiving routing instructions and beginning transit, the carrier determines its current location and optionally the direction needed to begin its route at step 502. In a general sense, a carrier can only move in two directions, forward or backwards and, in some embodiments, initiate a turn while moving. Because of the simplified movement model, a carrier can begin its transit even if it only has a rough understanding of its current location, such as by acquiring the current track section by RFID information. In some embodiments, the carrier uses more precise encoding in the track to determine its current location within a track section before proceeding.

Once the current position and necessary direction is determined, the carrier can begin transit at step 504. By using an understanding of the location on the track, geometry of the current track, distance to the next decision point, type of sample/payload, and current velocity, the carrier can determine a safe acceleration profile to begin transit. For example, if a carrier is a large distance away from the next decision point and is currently stopped, the carrier can begin accelerating at a maximum acceleration for the sample. In some embodiments, the acceleration of the carrier is ramped up to avoid exposing the sample to a high degree jerk.

Figure 10:
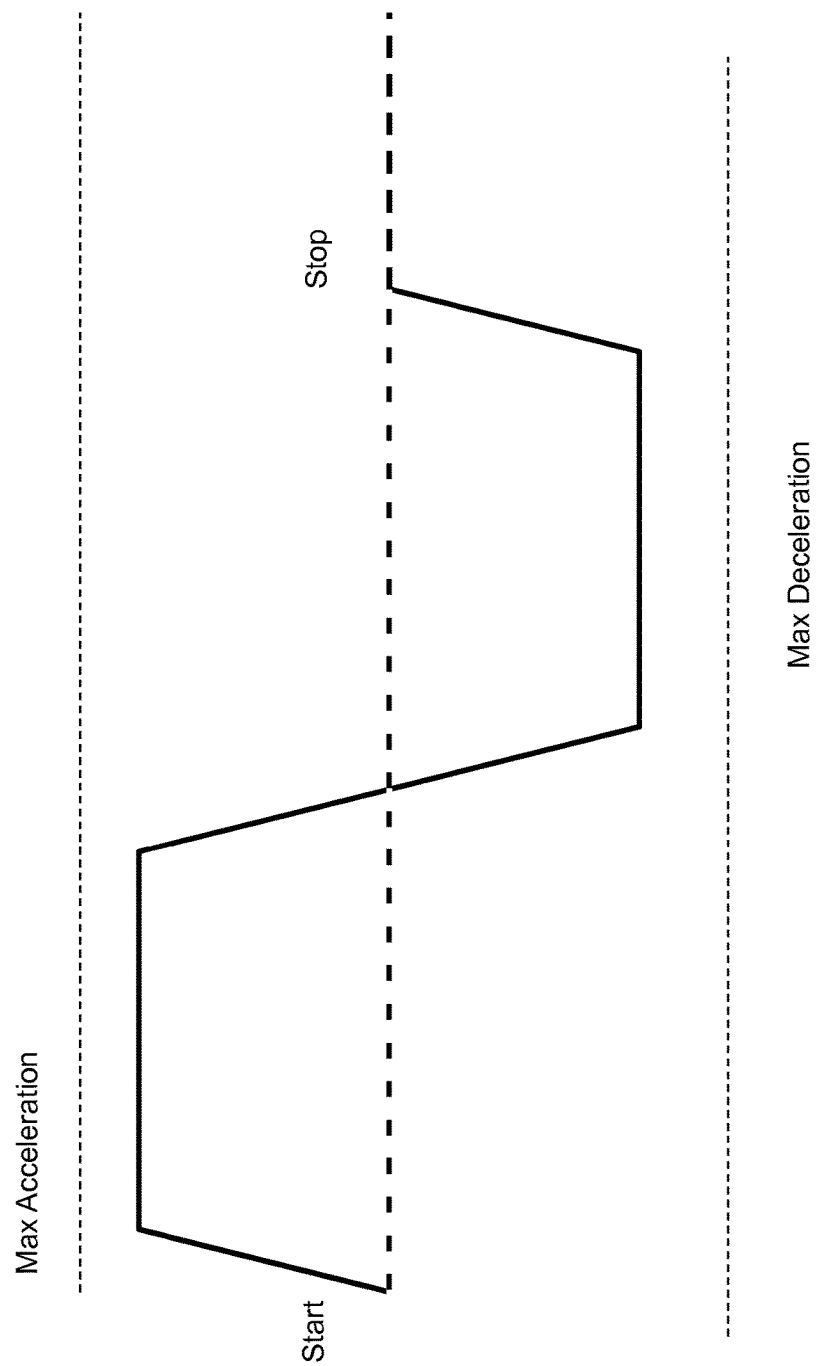
FIG. 10 is an exemplary acceleration profile used by sample carriers in certain embodiments.

FIG. 10 shows an exemplary acceleration motion profile that can be used to limit jerk and acceleration, while minimizing transit time. By using a trapezoidal acceleration profile, acceleration is ramped up to avoid unnecessary jerk until acceleration reaches a safe amount that is less than a threshold amount to avoid damaging or spilling the sample. By ensuring that acceleration is less than a threshold amount, a carrier may have some acceleration available to mitigate collisions or handle other unexpected situations without exceeding an acceleration threshold for the payload. Generally, maximum velocity will be reached midway between a start point and a stop point. In some embodiments, there is no top speed for a straight section of track, but curved sections of track are governed by a top speed to prevent excessive lateral acceleration. These speed limits and acceleration thresholds may be known to an intelligent carrier, and may be accessible in onboard memory. The exact motion profile used by a carrier can vary depending on the payload being carried. For example, empty carriers or carriers transporting reagents or non-sample payloads may utilize a motion profile that has higher limits than a motion profile that carries a sample.

Unlike traditional friction tracks, which are governed by a fixed velocity of the track, some embodiments of present invention can enable dynamic acceleration profiles and allow carriers to move at much greater average velocity than the prior art. In some embodiments, it is generally desirable to limit the maximum transit time between any points within the track system to less than a portion of an operation cycle of the clinical analyzer. For example, if the maximum distance between any points on a track system is 25 m and the operation cycle time is 20 seconds, it may be desirable to ensure that the average velocity of the carrier, including all turns, acceleration, deceleration, starting, and stopping, is sufficient to traverse 30 m in 5 seconds or less, or 6 m/s (~2.1 km/hr). Because a majority of the time in transit is spent accelerating or decelerating, it will be appreciated that the maximum velocity of the carrier on a straightaway can be substantially higher than this average velocity.

Because jerk and acceleration should be limited for samples, real-time control of acceleration is desired. This goal is furthered by giving control of acceleration to the carrier itself so that it can monitor its current trajectory using accelerometers or other sensors. The carrier can dynamically change its trajectory based on track conditions such as location, traffic, and the need to slow down for an upcoming turn. In this manner, the carrier can be responsible for monitoring and controlling its own dynamic stability conditions.

Referring back to FIG. 9, at step 510, the carrier determines whether or not it is safe to continue accelerating or decelerating in accordance with the trajectory determined in step 504. Step 510 can include collision detection or checking for other unexpected obstructions or a system-wide or carrier-specific halt command. In some embodiments, the decision at step 510 is based on collision detection sensors, including RF rangefinders, but can also include status information about the track received from the central management controller or from other carriers at step 505. This status information can include, for example, position and trajectory information about surrounding carriers or updated commands such as a halt instruction or new route instructions.

If the carrier determines at step 510 that it is not safe to continue with the planned trajectory, the carrier can take steps to mitigate or avoid a collision at step 512. For example, if it is determined that the acceleration profile will place the carrier dangerously close to another carrier, the carrier can begin slowing down. In some embodiments, the decision to slow down to avoid collision is based on an extrapolation of the current trajectory and the observed trajectory of the other carrier. If it is determined that the current trajectory will cause the carrier to come within an unsafe following distance from the carrier ahead of it, the mitigation procedure will be initiated. In some embodiments, each carrier is modeled as having a collision zone into which it is unsafe to enter. This collision zone moves with the carrier. If a carrier senses that it will invade a collision zone of another carrier (or another carrier will invade the instant carrier's collision zone), the carrier can mitigate the collision by decelerating (or accelerating to avoid a rear end collision in some embodiments).

After the carrier decelerates/accelerates to mitigate a collision, the carrier proceeds back to step 504 to determine an updated trajectory that takes into account the new collision avoidance conditions. If no unsafe condition is detected, the carrier proceeds with implementing its trajectory at step 514 (e.g., proceed with a portion of the trajectory before repeating steps 504-510 to allow for continuous monitoring of conditions). This can include accelerating or decelerating and observing track encoding and accelerometer information to determine its current status and trajectory. In some embodiments, the carrier will communicate its current status, including location, trajectory, and/or planned trajectory to the central controller and/or other carriers to assist in routing and collision avoidance at step 515.

As the carrier begins iteratively implementing its planned trajectory, it observes the track for upcoming landmarks, such as its terminal destination or an upcoming decision point at step 520. These landmarks can be identified via important features in the track, such as a warning or braking LED, by extrapolating the distance to a landmark from the observed encoding, or by some combination thereof. If no landmark is upcoming, the carrier continues to step 504 and continues iteratively calculating and implementing a planned trajectory.

In this example, there are two types of important landmarks. The first landmark is the destination of the carrier. The carrier can determine if it is nearing its destination based on track encoding or a landmark feature such as an LED and uses information to begin stopping or complete a stopping procedure at step 522. For example, a carrier may be instructed to stop at a precise location accessible to a pipette. This precise location may include an LED in the wall or floor of the track to assist a carrier in the stopping at a precise location with millimeter accuracy. In some embodiments, the calculated trajectory at step 504 is used to get a carrier in a rough location of its destination, while a stopping procedure at step 522 is used to determine the precise stopped location, such as by searching for a nearby LED landmark and stopping at the appropriate position.

Another important landmark is a decision point. Encoding or warning LEDs in the track can convey the position of an upcoming decision point to a carrier. For example, a central management controller may illuminate an LED at a braking position on the track some distance before a decision point to alert the carrier to decelerate to prevent unnecessary acceleration or collision at decision point. In other embodiments, the carrier extrapolates the relative position of an upcoming decision point from the track encoding and uses this distance to update its trajectory, if necessary, at step 524. At step 524, a carrier determines the relative location of a decision point and determines, based on its routing information, if the carrier will be turning or proceeding at the decision point. If the carrier will be turning, it may be necessary to update the trajectory to begin decelerating so that the velocity of the carrier is slow enough when it turns at the decision point to prevent unnecessary lateral forces that could harm or spill a sample.

In many instances, the carrier will be proceeding past the decision point without turning. In these instances, it may not be necessary to update the trajectory and the carrier can continue at its current velocity or even continue to accelerate through the decision point.

If the carrier determines that it needs to turn at the upcoming decision point, the carrier can slow down and initiate the turn at step 526. In some embodiments, the carrier is only capable of forward or backwards movement without assistance. In these embodiments, the carrier or central management controller can communicate with a switching mechanism at the decision point, at step 527, to ensure that any mechanical or electromagnetic devices in the track system 400 are engaged to direct the carrier in the appropriate direction when it traverses the decision point. Examples of devices in the track can include mechanical switches that block one path at a fork and assist the carrier in turning down the other path at the fork (like a railroad switch that can be mounted to rails or a gate when the track is shaped like a trough), magnets that pull the carrier in one direction or another, or changing signaling in the path that assists the carrier in turning, such as an LED that the carrier follows or an LCD or e-ink panel in the track that includes a line that can be followed by the carrier if the carrier is equipped with traditional line-following capabilities. Unlike prior art configurations that singulate, scan, and push individual carriers after they stop at a decision point, some embodiments of the present invention can negotiate a turn before a carrier physically arrives at a decision point. This can allow a carrier to proceed at a velocity limited by the curvature of a turn, rather than having to stop or wait for other mechanisms in order to turn.

In embodiments where a carrier has some steering capability and can turn at a decision point without the assistance of the next internal switch, the carrier can engage its steering mechanism to direct it to the appropriate path upon approaching the decision point. After turning at the decision point (or proceeding without turning) a carrier returns to step 504 to determine its next trajectory.

Virtual Queues

In some embodiments of the present invention, the reliable and rapid nature of the track system enables queues to be virtual, rather than physical. A virtual queue can be handled in software, rather than by physical limitations. Traditionally, queues have been physical. The simplest physical queue is effectively a traffic jam at any given part of a sample handling operation. A bottleneck creates a first-in first-out (FIFO) queue, where sample carriers are effectively stopped in a line, providing a buffer so that an analyzer or a decision point can request the next sample in the queue when it is ready. Most prior art lab automation tracks maintain FIFO processing queues to buffer samples that are waiting to be processed by the attached modules (analyzers or pre/post analytic devices). These buffers allow the track to process sample tubes at a constant rate, even though the modules or operator requests can create bursts of demand. FIFO queues can also substantially increase the throughput of the individual modules by allowing them to perform preprocessing tasks for future samples, for example, prepare a cuvette or aspirate reagent, while processing the current sample. While the rigid predictability of FIFO queues enables the parallelization of some processing tasks, it also can prevent the modules from using opportunistic scheduling that may increase throughput by reordering tests on samples to optimize resources. For example, the internal resource conflicts of most immunoassay analyzers can be so complex that the analyzers need to interleave the tests from multiple samples in order to reach maximum efficiency. A FIFO queue can reduce the throughput of these analyzers by as much as 20%. Another challenge with FIFO queues is their inability to handle priority samples (e.g., a STAT sample). If a STAT sample needs to be processed immediately, the entire FIFO queue has to be flushed back onto the main track, delaying all other samples on the track and forcing the original module to slowly rebuild its queue.

Another type of queue is a random-access (RA) queue. A carousel is an example of a physical RA queue found in analyzer modules. By aliquoting a portion of a sample into one or more vessels in a carousel ring, an analyzer module can select any of a number of samples to process at any time within the analyzer. However, carousels have many drawbacks, including added complexity, size, and cost. A carousel also increases the steady-state processing time, because a sample must be transferred into and out of the random-access queue. Processing delays depend on the implementation, such as the number of positions in a carousel. On the other hand, by having random-access to samples, a local scheduling mechanism within a module can process samples in parallel, performing sub-steps in any order it desires.

In some embodiments, carousels or other RA queues can be eliminated from the modules and the sub-paths (e.g., 210) from the automation system can be used as part of an RA or FIFO queue. That is, if the travel time for a sample between any two points can be bounded to a known time that is similar to that of a carousel, (such as predictably less than a portion of an operation cycle), the track 200 can be part of the queue for a given module. For example, rather than using a carousel, module 205 can utilize samples in carriers on sub-path 210. Preprocessing steps, such as reagent preparation, can be conducted prior to the arrival of a sample under test. Once that sample under test arrives, one or more portions of the sample can be aspirated into cuvettes or other reaction vessels for an assay. In some embodiments, these reaction vessels can be contained within module 205, off track, while in other embodiments, these reaction vessels can be placed in carriers on sub-path 210 to allow easy motion. If the sample under test is required to be at a module for longer than an operation cycle, or if multiple samples will be processed by the module during an operation cycle, the sub-path 210 can act as a queue for the module.

Furthermore, samples not yet under test, which may be currently located at other modules, can be scheduled for the next operation cycle. These next-cycle samples can be considered as residing in a virtual queue for module 205. A module can schedule samples to arrive during a given operation cycle for any sample on track 200. A central controller, or controllers associated with modules themselves, can resolve any conflicts over a sample for a given cycle. By giving a module prior knowledge of the arrival time of a sample, each module can prepare resources and interleave tests or portions of tests to more efficiently allot internal resources. In this manner, modules can operate on samples in a just-in-time manner, rather than by using large physical buffers. The effect is that the virtual queue for a given module can be much larger than the physical capacity of the sub-path serving that module, and existing scheduling algorithms can be used. Effectively, each module can treat track 200 as it would treat a sample carousel in a prior art module.

It should be appreciated that by employing virtual queues, in some embodiments, multiple modules can have multiple queues and can share a single queue or samples within a queue. For example, if two modules are equipped to perform a certain assay, a sample needing that assay can be assigned to a virtual queue for that assay, which is shared between the two modules capable of handling the assay. This allows load balancing between modules and can facilitate parallelism. In embodiments where reaction vessels are placed in carriers on track 200, an assay can be started at one module (e.g., reagents prepared and/or sample mixed in) and the assay can be completed at another (e.g., a reaction is observed at another module). Multiple modules can effectively be thought of as a multi-core processor for handling samples in some embodiments. In these embodiments, scheduling algorithms for the multiple modules should be coordinated to avoid conflicts for samples during a given operation cycle.

By employing virtual queues, modules can operate on samples while the samples are in the virtual queues of other modules. This allows low latency of samples, as each sample that is placed onto track 200 can be processed as quickly as the modules can complete the tests, without having to wait through a physical queue. This can greatly reduce the number of sample carriers on track 200 at any given time, allowing reliable throughput. By allowing modules to share queues or samples, load balancing can also be used to maximize throughput of the system.

Another advantage of using virtual queues is that STAT samples can be dynamically assigned priority. For example, a STAT sample can be moved to the head of any queue for the next operation cycle in software, rather than having to use a physical bypass to leapfrog a STAT sample to the head of a largely static physical queue. For example, if a module is expecting three samples to be delivered by track 200 for assays during the next operation cycle, a scheduler responsible for assigning samples to the module can simply replace one or more of the samples with the STAT sample, and have the track 200 deliver the STAT sample for processing during the next operation cycle.

Virtual queues can be accomplished by using software constructs to ensure the traditional rules of physical queues. Queues traditionally use a physical placement of samples to ensure that the samples will be able to behave as expected by a station served by the queue. A logical queue can be thought of as a contract. For example, a FIFO queue acts as a two-way contract between a station and sample. The sample agrees to be available when the logical slot assigned to the sample reaches the head of the queue. Meanwhile the station agrees to process the samples in order based on their position. This means that a sample can uphold its end of the bargain by doing anything else before it's logical position reaches the head of the logical queue. Traditional physical FIFO queues do not harness this caveat of queues, instead requiring the sample be physically proximate to the head of the queue until it is needed, such as by placing the sample onto a sidecar and gradually moving it forward as each sample ahead of it is processed. Using a virtual queue, a sample need not be physically proximate the interaction location of an instrument until it is needed. Accordingly, a sample may be placed in the logical queue well before it is physically able to reach the interaction point for the instrument, provided that the instrument does not need the sample to be available before the sample can be physically moved to that location. For FIFO queues, the determinability of when the sample will be needed can make this fairly simple for a processor to guarantee.

Random-access queues behave slightly differently. The contract formed between a sample and an instrument in a random-access queue is that the sample agrees to be available upon request by the instrument. In a pure random-access queue, the instrument does not guarantee anything in exchange. However, in some embodiments, the basic workflow within an analyzer can be examined to provide some limitations on when a random-access queue will need access to a sample. For example, unlike software instructions that may include branch execution, typical workflows within an analyzer do not result in dependent steps (e.g., testing) that varies based on the results of a prior step. In embodiments where the order of testing is dependent on the outcome of tests, the amount of time between that test and the need for subsequent tests may be sufficient to allow the automation system to handle a sample appropriately. In this manner, there may be limitations on when a sample may be needed at the physical location of the head of the queue, while the sample is in that logical random-access queue. This may provide options for handling the sample within the automation system before the sample may be needed at the head of random-access queue.

Similarly, in some embodiments, processing within a station can be scheduled several instrument cycles in advance. This may be because a processor directing a workflow within an analyzer can operate faster than the samples can physically be processed. For example, a scheduling algorithm may utilize a model of workflow in an analyzer that can be fully analyzed by a processor within milliseconds, whereas the actual workflow the analyzer may take several minutes. Accordingly, in various embodiments, random-access queues may not be fully random-access, as the identity of samples within the random-access queue that may be required at each cycle of an instrument may be limited to only a subset of samples within a random-access queue. For example, a random-access queue with 10 samples may only need one of five samples for any given operation cycle, which may be determined and scheduled before a sample is even placed in a queue or moved by an automation system away from a location physically proximate the head of the queue.

A FIFO queue may have the following workflow characteristics, which may be considered in software operating a virtual FIFO queue:
  the samples in the queue are made available to the module in a fixed order;
  once a sample has been made available, it will not be requested again;
  samples are automatically removed from the queue once they reach the head;
  the Nth sample in the queue will not be requested by the module for at least (N×a station cycle time) seconds; and
  in order to process a priority sample, the entire queue should be flushed.

A random-access queue may have the following qualities, which may be considered in software operating a virtual random-access queue:
  the samples in the queue can be requested by the module in any order;
  a sample may be requested multiple times; the module must explicitly release a sample from the queue;
  Any sample in the queue can be requested by the module, and a requested sample must be made available to the module within the cycle time of the requesting station; and
  a priority sample can be added to the queue at any time (however, the priority tests may not need to be processed by the analyzer until the already-started scheduled tests are processed.)

Software operating on a processor, such as central controller 440 can communicate with other processors that control local queues to determine timing requirements for each sample that may be placed into those queues. By utilizing knowledge of the timing of the automation system and the local queues, software managing virtual queues can assign samples to a queue without directing the sample to the physical location of this station utilizing the queue, until it is ready. For example, if central controller 440 understands that a sample will be needed in 35 seconds at the head of a FIFO queue at one location in the analyzer, controller 440 may schedule other tasks for that sample in the intervening 35 seconds. Similarly, if a central controller 440 learns that a sample to be added to a random-access queue may be needed in five machine cycles, controller 440 may add the sample to that local random-access queue whenever current traffic limitations ensure that the sample can be available within five machine cycles. Similarly, provided the automation system is fast enough, social controller 440 can guarantee that a sample can meet the requirements for random-access queue when it is anywhere else in the automation system, provided that no other station demands access to the sample during the same machine cycle for which the sample will be requested at the head of the random-access queue.

Virtual queues may be assisted by utilizing a central controller that assigns samples to each local queue for each local module. Software operating on a central controller can then dictate which samples are placed into which queues when. This may also allow a central authority to oversee any potential conflicts. Central controller can also work with a sample handling module or sample manager modules that are responsible for placing samples onto an off of the automation track. This can be useful for limiting the overall traffic on the system, allowing performance requirements to be maintained. This can allow samples to reliably be moved to stations to fulfill the contracts of the virtual queues.

System-level routing software can attempt to process all of the samples as quickly as possible by distributing the samples to the processing modules. This software can maintain a model of the maximum amount of time needed to reliably move a sample from a current location to a location in the system associated with the head of a queue (e.g., the pipette or handling arm location for a given station).

In some embodiments, this model can be simplified by utilizing automation mechanisms whereby any sample that is placed in a station's logical clue may be moved from a current position in the IVD equipment in less than one system cycle time. The system cycle time can be a unit of time used by the automation system that defines the rate at which samples will be moved between positions in the system. That is, a system cycle time identifies the maximum transit time between any points within the track system that the sample will be succeedingly scheduled. For example, if the maximum distance between any points on a track system (for which the sample might be ensuingly scheduled) is 25 m, the operation cycle time for the automation system might be 20 seconds. If all samples remain with a distance that can be covered within an operation cycle of the automation system (e.g., 25 m), the automation system can guarantee that the sample can be placed at the head of the queue on demand (e.g., when it reaches the head of the logical queue).

Module cycle time is the amount of time required by a module/station to complete its processing of a given sample. Automation transit time is the amount of time needed for a sample to move from one location to another. For example, if a sample is scheduled to be used by two module stations during successive system cycles for the analyzer, the central controller would need to ensure that the module cycle time, plus the transit time is less than the system cycle time. If a sample is idle prior to being requested, the central controller may simply need to ensure that the transit time is less than the system cycle time. This allows a station to request any sample in its queue, knowing that it will arrive when needed, regardless of whether the sample is physically proximate the station or several meters away, or even being processed by another station. In this example, a requesting station will request a single sample each system cycle.

This balance can occur when the minimum cycle time (e.g., the rate at which it will request samples) of the requesting station is substantially the same or greater than the operation cycle time of the automation system. Provided the requesting station notifies the controller of the automation system that it needs the sample with a sufficient fraction of a system cycle time to allow the automation to transit the sample to the station, this balance can be maintained.

This may also be accomplished when the maximum allowable wait time (e.g., the maximum allowable amount of time between when a sample is requested from the automation system and when the sample is needed) is the same or greater than the automation system cycle time (plus any additional transit time needed, in embodiments where the automation system is too large to ensure that the system cycle time is greater than the maximum module cycle time for the preceding station, plus the needed transit time). For example a station can know the identity of the samples that will be needed a few module cycles ahead of time (or at least at the beginning of a single system cycle, with enough time to allow a sample to transit the distance needed on the automation system). If this balance is met by the control of the central controller, any sample on the transport mechanism that is placed into a logical queue in software can meet the requirements previously defined for a sample in either a FIFO or RA queue. This means that the physical implementation of either type of virtual queue is simply a single processing position in front of a module. The rest of the samples "in the queue" can be anywhere on the transport mechanism, in some embodiments. In some embodiments, such as in large automation systems with many modules, the samples in a queue can be anywhere within the nearby modules, allowing transit time requirements described above to be maintained, even if the transit times for the entire system is greater. This can allow more scalable systems, as nearby modules can act as work cells, sharing samples within their queues without requiring samples to continuously go from one side of the automation system to the other.

By maintaining guarantees that samples can be physically placed at the head of the queue upon request by a station, a central controller can utilize the automation system itself as a constantly moving physical space for the samples within a logical queue. The central controller can maintain software structures that ensure these constraints and can be responsible for assigning samples to queues to ensure these constraints are met. The central controller can treat different queues differently. For example, sample handling stations, such as decappers can be FIFO queues that do not require a certain order of samples. Accordingly, central controller may send samples to head of this queue in any reasonable order, which may allow the central controller to ensure that samples are ready for subsequent handling by other stations, for which that sample may have been placed into a queue. Similarly, the central controller can be charged with moving samples that are idle, but waiting for their turn in a queue, to suitable locations within the automation system to act as temporary physical storage. This can be in active track sections, dedicated storage areas, etc.

By distinguishing the logical model for a queue from the physical location of the sample, queues may be managed in software. Managing queues in software provides certain advantages that may not be practical for prior art physical queues. For example, software queues may be managed and rearranged instantaneously. This may allow a processor that is managing a queue to determine the identities of samples within the queue, look up the test panels needed to handle the samples, such as by requesting this information from a laboratory information system, determine the availability of stations for carrying out the steps required by the test panels for each sample, interleave the tests and steps for each sample to optimize performance and minimize down times of any stations, schedule preparation of any reagents necessary for tests ahead of the physical arrival of the sample at a testing station, and thereby determine appropriate queues for each sample and approximate or determine when that sample will be needed by each station within the analyzer. This entire process may take place in the course of milliseconds or quicker.

When a STAT sample arrives, queues may quickly be rearranged to accommodate the higher priority of the stat sample without requiring any physical movement of pending samples in those queues. In software, the steps to be taken on the samples can be reordered, without ever physically affecting the samples, other than by altering the cycle in the future in which that sample will be required at a given station. For example, the size of queues may be dynamically configurable in software. Whereas prior art FIFO queues required physically flushing a queue to change the physical order of samples to allow a stat sample to move to the head of the queue ahead of those samples ahead of it, changing the order of samples in a FIFO queue maintained in software can be a trivial matter. The position within the queue associated with each sample can merely be shifted by one, allowing the STAT sample to occupy the next position in the queue to be processed. Similarly, whereas random-access queues were typically limited in the prior art, based on physical constraints, due to scalability problems of physical systems utilized to allow random access to samples contained therein, such as carousels, random-access queues maintained in software may be dynamically configurable. For example, a random-access queue may have five normal priority samples when a STAT sample arrives. A sixth position may be created in the queue in software to accommodate the STAT sample. A processor maintaining the queue and scheduling interaction between a pipette and samples within the queue can be alerted to the presence of the stat sample, allowing the processor to schedule the stat sample to be the highest priority sample to be accessed within the queue. The pipette may request the STAT sample before the normal priority samples in that queue without ever physically affecting those samples that might otherwise be temporally displaced.

Figure 11:
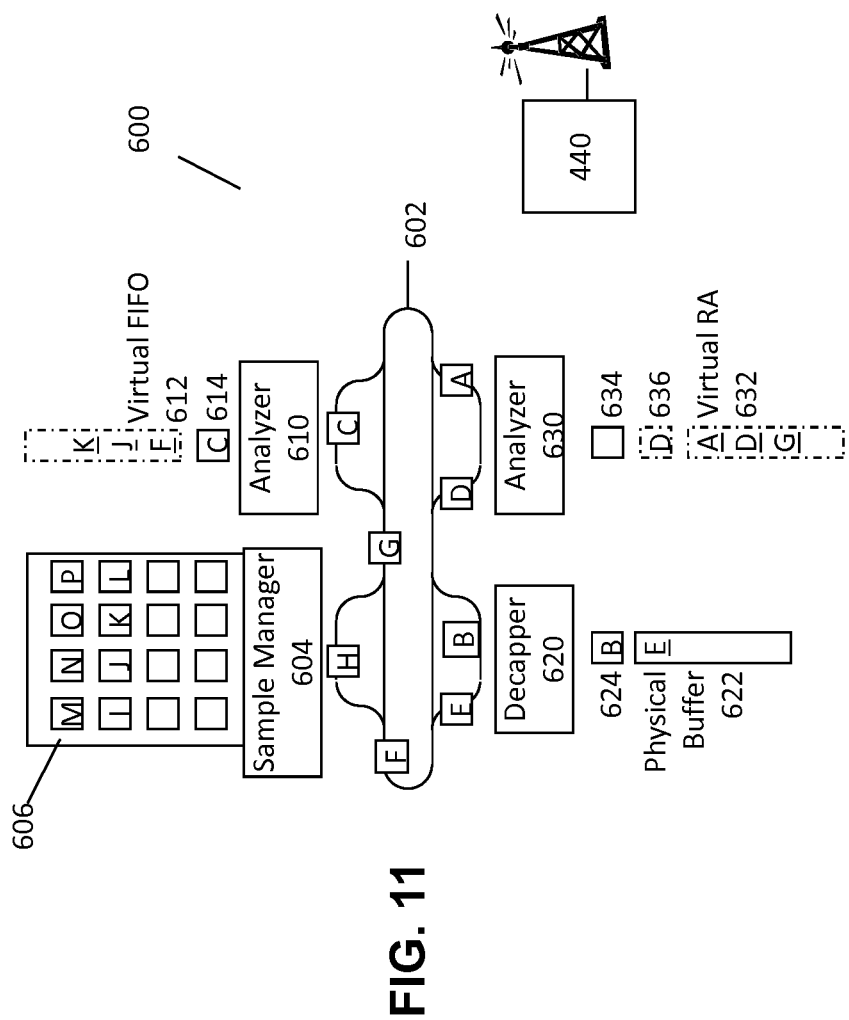
FIG. 11 is a diagrammatic view of an exemplary automation system utilizing virtual queues that can be used with certain embodiments.

FIG. 11 shows an exemplary analyzer system 600 that includes four modules, a sample manager 604, a first analyzer station 610, a decapper station 620, and a second analyzer station 630. The stations are serviced by an automation track 602 that includes a plurality of sidecars its service the individual stations. Within analyzer 600, a plurality of samples A through P are processed. A combination of physical buffers and virtual queues can be used to facilitate processing of the samples. The selection of queues used in system 600 is merely illustrative and it should be appreciated that any combination of virtual queues and physical buffering may be utilized. In some embodiments, all queues are virtual. Sample manager 604 illustrates the use of physical space off of the automation system that is used to store samples. Samples I through P may be placed in tray 606, allowing those samples to be ordered and held for long-term storage. Trays of samples may be placed into and taken out of analyzers providing a simple mechanical interface for manipulating samples by an operator. Sample manager 604 can process samples stored in these trays in any reasonable manner, effectively treating these as random-access or FIFO queues that are off of the automation track. Samples may be removed from these trays and placed onto the automation track to begin processing. Samples undergoing processing may be moved by sample manager 604 back into locations within the tray 606. Accordingly, tray 606 may be distinguishable from buffers and virtual queues that are on automation track 602 and local sidecars. In this example, sample H has recently been processed by sample manager 604, placing sample H onto automation track 602.

Within the situation shown in FIG. 11 system 600 includes samples A through H on automation track 602, while samples I through P remain in tray 606, awaiting processing by sample manager 604.

Analyzer 610 maintains a virtual FIFO queue 612, by utilizing the principles discussed throughout. In this example, virtual FIFO 612 includes three samples that are located within the logical structure of virtual FIFO 612, samples F, J, and K. Sample C is placed in position 614 within virtual FIFO 612, which corresponds with the head of the queue, meaning that that sample is currently being processed by analyzer 610. As can be seen, sample C resides on the sidecar associated with analyzer 610 at a position suitable for interacting with analyzer station 610. By way of illustration, samples J and K are not currently on automation track 602. However, samples J and K will not be needed by analyzer 610 for at least two more system cycles. Samples C and F must be processed first according to the rules of a FIFO queue. A controller that schedules samples within the various queues, including adding or removing the samples, such as central controller 440, can take note of this relationship. Controller 440 can communicate with sample manager 604 to determine that samples J and K will be available for processing on automation track 602 within the next two system cycles. Accordingly, provided sample manager 604 operates within normal parameters, analyzer 610 can access these samples on time. Accordingly, virtual FIFO 612 allows analyzer 610 to logically schedule the samples for future interaction. Analyzer 610 may not even know that samples J and K are not presently located on automation track 602. In some embodiments, system 600 may maintain a degree of fault tolerance, whereby analyzer 610 may simply skip a cycle in a fault tolerant mode if a sample manager 604 is unable to provide samples J or K in the scheduled manner. This may cause a small, one-time delay that is overcome by the typical advantage of using virtual queues more efficiently than physical queues.

Decapper 620 maintains a physical queue 622. This physical queue acts as a buffer for samples in the automation system. As can be seen, sample B, at the head of the physical queue, at logical position 624, resides on a sidecar associated with the capper 620. Meanwhile, sample B also resides on that sidecar as part of the physical buffer created by that sidecar. The sidecar and the physical queue 622 have one to one correspondence, allowing physical queue 622 to be both a logical and physical buffer. In some embodiments, decappers 620 may operate without any guaranteed performance requirements, allowing decappers 620 to consume samples in any order, at any suitable pace. Meanwhile, samples within a physical buffer 622 may be unable to be scheduled in any other virtual queues because controller 440 cannot guarantee that it can meet the implied contract of placing a sample in a queue.

Analyzer 630 maintains a virtual random-access queue 632. Analyzer 630 may be serviced by a sidecar off track 602. In this example, analyzer 630 has just finished performing a step on sample A. Accordingly, the physical slot 634 that corresponds to the "head" of the queue (e.g., the sample currently being used) is unoccupied as sample A has left that physical location and is returning to the virtual random-access pool (e.g., the logical pool of queue 632 and the physical location of wherever on track 602 controller 440 places the sample). Meanwhile, analyzer 630 has requested another sample, sample D.

Virtual queue 632 includes for samples, which are, in this example, all readily available on track 602. Virtual queue 632 also maintains an identity 636 of the next sample to be moved into position to physical position 634 for interaction with analyzer 630. Position 634 may be a position corresponding to a pipette, allowing analyzer 630 to aspirate portions of the sample. In this example, sample A returns to the general pool of virtual queue 632, and is placed back onto track 602, leaving position 634. Sample D has been requested by the analyzer by communication with central controller 440. Accordingly, sample D occupies logical position 636, identifying it as the next sample to be processed. In some embodiments, a local processor within each analyzer is responsible for making local queue decisions, while controller 440 is responsible for moving samples into physical position to meet the requirements of the queue and for selecting which samples can be scheduled to be placed into each queue.

In this example, to simplify traffic management, no samples are placed into two virtual queues. This may be a simple way to guarantee that there are no conflicts between analyzer 610 an analyzer 630. For example, if sample F was placed into both virtual queues 612 and 632, it may be possible for both analyzers 610 and 630 to request sample F during the same system cycle, creating a conflict. In some embodiments, samples may be placed into multiple queues, but queues may need to be fault tolerant, allowing a module to skip a cycle should a conflict occur, or software that arbitrates conflicts must be applied. For example, software operating on processor 440 may be able to negotiate reorganization of virtual FIFO 612, giving priority to virtual queue 632 (or vice versa). Analyzer 610 may have mechanisms sufficient to prepare for samples F and J prior to requesting either of these samples. Accordingly, analyzer 610 may be able to tolerate a change in the order of virtual FIFO 612 at the request of central controller 440.

Scheduling rules maintained on a processor, such as controller 440 can be utilized to avoid conflicts between queues. Queues can be given priority over other queues, for example, allowing controller 442 choose which queue a sample should first be placed into. Workflow may also dictate this. For example, rules may be established in software that identify queues associated with preprocessing stage in as necessary before placing samples into queues associated with processing stations. Rules can also dictate whether or not samples can be placed into multiple queues and what to do in the event of conflicts should a sample be placed into multiple queues. In the example where samples are allowed to exist in multiple queues simultaneously, certain rules and software can identify the requirements for minimizing conflicts and ensuring that potential conflicts to not treat errors in the system. For example, each queue can be defined as having certain set up and hold times for samples, as well as identifying the guarantees that must be made. For example, a critical queue can be identified as requiring an absolute guarantee that controller 440 can deliver a sample of the queue on demand. Meanwhile, other stations may be much more tolerant. For example, a virtual queue assisted of the decapper may not care which order it receives samples, allowing it to request a replacement sample should the currently requested sample be unavailable.

By utilizing rules in software, queues maybe dynamically configurable. Rules may alter how stations interact with samples, allowing remote configuration or changing configuration to deal with requirements of the lab and current conditions. For example, analyzer 630 may be configured to have a virtual queue when configured to perform certain tests during one shift a lab, but then be configured to utilize a virtual FIFO queue during another shift of the lab. Similarly, as more efficient scheduling algorithms are developed, these algorithms can be utilized to change the way in which queues interact through software updates, without requiring hardware changes.

Rules may take advantage of workflow within an analyzer to provide guidance to avoid conflicts between queues. For example, overall throughput of the system may be reduced by placing a sample simultaneously in a FIFO queue for a preprocessing station and into a FIFO queue for a processing station, such as an analyzer testing station. Rules can be utilized to identify the need for causal relationships between these queues. For example, a sample may be placed in the FIFO queue of the a decapper station such that it is near the head of the queue, while also being placed into a FIFO queue for an analyzer station provided that the sample will reach the head of the analyzers FIFO queue after it has been processed by the decapper. This ensures that the sample arrives at an analyzer station without a cap. By considering the order of operations, the sample may be placed into both of these queues in such a way that the sample is processed almost immediately after being de-capped. This may be useful for minimizing the amount of traffic in the automation system, as idle samples add to congestion. By placing samples into multiple queues with rules to limit conflict and to ensure performance criteria, samples may be handled within an analyzer in an efficient manner, minimizing downtime of each sample once placed in the automation system.

Placing a sample into multiple random-access queues (or a FIFO queue and a random-access queue) may be more challenging. One way that this may be accomplished is by applying fault tolerant rules to shared samples. For example, the guarantee of the queue, that a sample in the queue be available at any time it is requested, may be broken if two stations request the sample during the same operation cycle. In some embodiments, stations can be configured to handle this potential conflict. In some embodiments, a station may simply postpone its request if it conflicts with another station, moving to the next sample for processing, if feasible. In some embodiments, a station may simply skip a cycle, waiting an additional cycle to receive the conflicted sample. This may be suitable in systems where conflicts are rare. The overall performance advantages of allowing samples to be shared in multiple queues may generally provide a performance advantage that overshadows the occasional inefficiency of missed cycles due to conflicts. The central controller can act as an arbiter to resolve these conflicts. In some embodiments, the central controller can avoid these conflicts entirely by ensuring that no samples appear in multiple virtual random-access queues (or a single virtual random-access queue and any other queue).

In some embodiments, advanced modeling of the need for samples can resolve conflicts of samples shared between multiple queues. It should be appreciated that once the samples in a lot (e.g., a new tray) have been identified, the central controller for an analyzer can retrieve the test panels for each of these samples from a laboratory information system. The test panels for the samples provide a roadmap of all of the tasks that must be performed to process all of the samples in the lot. The central controller can then retrieve an identification of which stations within a multi-module analyzer can accomplish each of the steps in the test panels. The analyzer may then run the scheduling algorithm to identify a schedule that accommodates all of the test panels utilizing the multiple stations, without requiring multiple samples be at multiple stations at the same time. This schedule can take into account transit times within the automation system, and may also build in buffers and contingencies into the schedule, such that an error in one sample that causes a delay in one station can be overcome by rescheduling samples, or by allowing fault tolerant downtime of one or more stations.

By utilizing a predetermined schedule that may be calculated and modeled in software before samples are processed, a central controller can model and avoid conflicts, before samples are scheduled and placed into any queues. Similarly, during operation of testing of a lot, any deviations from the schedule can be reported to the central controller, allowing the central controller to rerun a scheduling algorithm to account for the deviation. For example, if a first testing station encounters an error that will require one or more operation cycles to recover, the central controller can determine a new schedule that accounts for this downtime. For example, the new schedule may note that a nearby station has redundant capabilities with the delayed station. Samples previously placed into the queue for the delayed station may be placed into a queue associated with the redundant station in software. In this manner, samples may be rerouted on-the-fly within fractions of a second, without requiring samples to be physically moved from one physical queue to another physical queue. The time required to reschedule samples may be limited by the processor, rather than physical movement of the automation track. This rerouting and rescheduling can occur while samples continue to move on an automation track.

In some embodiments, the scheduling tasks described herein can be divided between multiple processors. For example, a central controller can be responsible for assigning samples to a queue, while a local processor associated with a station or module can manage that queue. To assist a central controller in scheduling samples and placing them into queues in software, the local processors may report back an expected schedule for processing of the samples within their queues. For FIFO queues, this information may be reported as a fairly well-defined order, allowing the central controller to have a precise idea of when samples will become available when needed by the queue. Random-access queues may also report this information in a precise manner to central controller, in some embodiments. In some embodiments, random-access queue controllers can also report information in a manner that balances the requirements. For example, upon receiving a notification that a sample requires a certain immunoassay to be provided by station, a local processor for that station can report to the central controller that it will take five machine cycles to prepare the reagents for the test, after which it will need the sample for the immunoassay at some point within the following five machine cycles. A central controller can utilize this information to allow the sample to be placed into other virtual queues for processing, accounting for the constraints reported by the random-access queue manager for the station that will be handling the immunoassay.

FIG. 12 illustrates exemplary steps for utilizing virtual queues within an automation system. Method 650 includes steps that may be carried out by one or more processors in an analyzer. For example, a central controller can be responsible for some or all of these steps. Some of the steps may be optional. Some of the steps may also be carried out by local module processors within the analyzer. At step 652, a processor receives the identities of samples in the analyzer. This can occur through any of the mechanisms described throughout. For example, as each barcode of each sample is read when a sample is placed into a carrier, the identity, and possibly location information, for that sample can be communicated to a processor overseeing the automation system. At step 654, using identities of the samples, the test panels needed for those samples can be determined by retrieving test panels from a laboratory information system or other database. At step 656, the processor analyzes the retrieved test panels and identifies the steps within the analyzer needed to complete the test panel for each sample. At step 658, the processor determines which stations can perform the tasks necessary to complete the test panels. Using this information, the processor can determine the functional rules that place constraints on handling samples. For example, if a sample needs immunoassays, and only a single immunoassay station is available, the processor can determine that the sample must be routed to that station at some point during processing. The processor may also utilize test panels and a model of workflow to determine the order in which steps must occur. For example, the processor may determine that all samples must be de-capped prior to processing.

At step 660, the processor assigns samples and tasks to stations. Once the tasks needed are determined and the capabilities of each station are considered, the processor can match capabilities with needs. At step 662, the processor determines a desired queue for each module. The desired queue can include an identification of the type of queue, such as random-access or FIFO, the order of samples to be placed in each queue, and an identification of any time constraints. Once a schedule is accepted, a model of each of these queues can be maintained in memory associated with the processor, creating a virtual queue. Each virtual queue can have a plurality of samples assigned by the processor and one or more processors can schedule the order of samples in that queue. An example of managing samples in a virtual queue can be seen in the virtual queues in FIG. 11.

At step 664, the processor determines a module cycle time for each module. This may be used to determine when a sample may be processed within each queue, as well as to identify any transit time limitations that need to be considered. Module cycle time may include a length of time needed by the module to process at least one sample. At step 666, the timing and queue assignment information is considered to determine an overall schedule for all samples within a plurality of stations. This may be useful for determining which samples will be utilized where. In some embodiments, the scheduled tasks may predetermine all tasks to be carried out by a plurality of stations within the next several operation cycles for the automation system and the stations. In this manner, all queues can be predictably handled. For example, whereas a traditional random-access queue may access samples in any arbitrary order, based on the schedule of tasks determined at step 666, the order in which a virtual random-access queue utilizes samples may be predetermined well before samples are positioned in physical proximity to a station.

At step 668, the processor determines if the scheduled tasks determined in step 666 includes any potential conflicts. For example, a processor may determine whether or not transit time constraints of the system allow samples to meet the schedule. The processor may also consider whether any two stations require samples simultaneously. If so, method 650 returns to step 662 determine a different schedule. During this step, conflict may be resolved, for example, by assigning a priority level to each module or station and comparing the priority levels to choose a schedule that resolves the conflict. At step 670, a processor may optionally determine whether or not the determined schedule meets a performance threshold or may be considered an optimal schedule. For example, a performance threshold may define a maximum number of down cycles for each station, a maximum turnaround time for samples, or any other performance criteria that may be useful in determining whether the schedule is acceptable. If the schedule is not acceptable, method 650 returns to step 660. If the schedule is acceptable, at step 672, the processor stores the schedule and memory. The schedule will then be used in subsequent physical handling of samples.

At step 674, the processor facilitates placement of each sample within the automation system to satisfy determined queue for each module, based on the schedule. Each sample is placed within the automation system at locations that satisfy the transit time criteria necessary to satisfy the schedule. Transit times, traffic patterns, modules cycle times, etc. may all be considered in step. At step 676, the automation system provides samples to each module at determined times, according to the schedule. At step 678, if there are no errors, steps 674 and 676 repeat, implementing the schedule and moving samples into and out of physical proximity with the stations necessary to process the samples. If an error occurs at step 678, the processor may repeat steps 660 through 672 to develop a new schedule utilizing the virtual queues that overcomes the encountered error. An error may include for example an unexpected missed machine cycle for a station due to a physical blockage, malfunction, unexpected sample error, etc.

Embodiments of the present invention may be integrated with existing analyzers and automation systems. It should be appreciated that carriers may be configured in many shapes and sizes, including layouts and physical configurations suitable for use with any contemplated analyzer or instrument. For example, in some embodiments, a carrier may include multiple slots for carrying multiple samples around an automation track. One embodiment, for example, may include a physical layout of a tube-holding portion of a carrier with multiple slots in one or more transport racks. Each rack may include multiple slots (e.g., five or more slots), each slot configured to hold a tube (e.g., a sample tube).

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. A method of implementing queues for an automation system comprised of a plurality of analyzer modules connected to one another by an automation track, each of the plurality of analyzer modules configured to each perform at least one assay on sample tubes, the automation track configured to transport the sample tubes between the plurality of analyzer modules within a maximum transit time, the method comprising:
   determining a desired queue for each analyzer module, wherein the desired queue comprises an ordering of a plurality of sample tubes to be processed by the analyzer module;
   determining a module cycle time for each analyzer module, wherein the module cycle time comprises a length of time needed by the analyzer module for processing one of each of the plurality of sample tubes and that length of time is greater than the maximum transit time;
   placing each sample tube in the automation track from its current location to satisfy the desired queue for each analyzer module, wherein each sample tube is placed to reach the analyzer module at a determined time based on the ordering of each sample tube in the desired queue and the module cycle time;
   providing each sample tube to each analyzer module at the determined time; and
   aspirating a portion of each sample tube by each analyzer module, upon arrival of the sample via the automation system, and performing at least one assay on the aspirated portion, wherein the automation system further comprises one or more holding buffers, and each of the plurality of analyzer modules comprises a module holding area, where the holding buffers and holding areas are configured to hold more than one of the plurality of sample tubes, and wherein the desired queue for each analyzer module is configured to include sample tubes that are in the desired queues and the one or more holding areas of other modules.

2. The method of claim 1, wherein the step of placing comprises moving each sample tube to at least one of: (i) a location along the transport mechanism, (ii) at least one of one or more holding buffers, (iii) at least one of a plurality of module holding areas, and (iv) another of the plurality of analyzer modules.

3. The method of claim 1, further comprising:
assigning a priority level to a first module of the plurality of analyzer modules;
comparing the priority level of the first module to that of a second module of the plurality of analyzer modules upon occurrence of a conflict for each sample tube between the first module and the second module; and
providing the at least one sample tube to the first module or the second module based on the compared priority level.

4. The method of claim 1, further comprising:
moving each sample tube in the automation system to account for a STAT sample, wherein the movement of each sample tube allows for the desired queue to be satisfied after processing of the STAT sample; and
providing the STAT sample to the module for processing thereof.

5. The method of claim 1, wherein at least a subset of the plurality of analyzer modules comprises at least one of an immunoassay module and a clinical chemistry module, and wherein the at least one sample tube comprises a patient sample.

6. The method of claim 1 further comprising, receiving at least a subset of the plurality of sample tube at a sample handling module configured to add and remove the at least one sample to and from the transport mechanism.

7. The method of claim 1, wherein the desired queue comprises one of a first-in first-out queue or a random-access queue.

8. An automation system comprising:
a plurality of analyzer modules, each configured to each perform at least one assay on sample tubes, each analyzer module comprising a module holding area configured to hold one or more of the sample tubes and a pipette to aspirate a portion of a fluid sample from each sample tube, wherein the at least one assay is performed on the aspirated portion;
an automation track configured to transport the sample tubes between the plurality of analyzer modules within a maximum transit time, the automation track connecting the plurality of modules to one another; and
a schedule controller configured to process instructions to implement the method of:
determining a desired queue for each analyzer module, wherein the desired queue comprises an ordering of at least one sample tube to be processed by the analyzer module,
determining a module cycle time for the analyzer module, wherein the module cycle time comprises a length of time needed by the analyzer module for processing one of the at least one sample tube and that length of time is greater than the maximum transit time,
placing the at least one sample tube in the automation track from its current location to satisfy the desired queue for the analyzer module, wherein the at least one sample tube is placed to reach the analyzer module at a determined time based on the ordering of the at least one sample and the module cycle time, and
providing the at least one sample tube to the analyzer module at the determined time; and
one or more holding buffers configured to hold more than one of the at least one sample tube, wherein the transport mechanism connects the one or more holding buffers with the plurality of analyzer modules,
wherein the desired queue for each analyzer module is configured to include sample tubes that are in the desired queues and the one or more holding areas of other modules.

9. The automation system of claim 8, wherein placing comprises moving the at least one sample tube to at least one of: (i) a location along the transport mechanism, (ii) at least one of one or more holding buffers, (iii) at least one of a plurality of module holding areas, and (iv) another of the plurality of analyzer modules.

10. The automation system of claim 8, wherein the schedule controller is further configured to process instructions to implement the additional method of:
assigning a priority level to a first module of the plurality of analyzer modules;
comparing the priority level of the first module to that of a second module of the plurality of analyzer modules upon occurrence of a conflict for the at least one sample tube between the first module and the second module; and
providing the at least one sample tube to the first module or the second module based on the compared priority level.

11. The automation system of claim 8, wherein the schedule controller is further configured to process instructions to implement the additional method of:
moving the at least one sample tube in the automation system to account for a STAT sample, wherein the movement of the at least one sample tube allows for the desired queue to be satisfied after processing of the STAT sample; and
providing the STAT sample to the module for processing thereof.

12. The automation system of claim 8, wherein at least a subset of the plurality of analyzer modules comprises at least one of an immunoassay module and a clinical chemistry module, and wherein the at least one sample tube comprises a patient sample.

13. The automation system of claim 8, further comprising a sample handling module configured to add and remove the at least one sample tube to and from the transport mechanism.

14. The automation system of claim 8, wherein the desired queue comprises one of a first-in first-out queue or a random-access queue.

15. An analyzer for use in in vitro diagnostics, comprising:
an automation system configured to transport patient sample tubes;
a plurality of analyzer stations, each having a pipette configured to aspirate portions of patient samples in the patient sample tubes transported by the automation system once each tube arrives at each analyzer station and to each perform at least one assay on the aspirated portions, wherein each of the plurality of analyzer stations processes samples at a rate slower than a maximum transit time of the automation system; and one or more processors configured to:
- maintain a plurality of queues, including at least one FIFO queue, for at least a subset of the plurality of analyzer stations in memory; and
- assign a plurality of the patient sample tubes to each of the plurality of queues, wherein patient sample tubes assigned to each of the plurality of queues need not be located physically proximate to an analyzer station associated with each of the plurality of queues, and wherein each of the plurality of queues includes patient samples that are also assigned to other of the plurality of queues.

16. The analyzer of claim 15, wherein the one or more processors are further configured to assign individual objects to multiple queues simultaneously.

17. The analyzer of claim 15, wherein the one or more processors are further configured to verify that each object can physically reach the analyzer station associated with each of the plurality of queues to which the patient sample tube is to be assigned within a time period needed by the queue.

18. The analyzer of claim 15, wherein the plurality of queues include at least one random access queue.

* * * * *